(12) United States Patent
Ghosh et al.

(10) Patent No.: US 8,594,775 B2
(45) Date of Patent: Nov. 26, 2013

(54) TECHNIQUES FOR DETERMINING MORPHOLOGICAL STABILITY OF CARDIAC CYCLES

(75) Inventors: Subham Ghosh, Circle Pines, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 84 days.

(21) Appl. No.: 13/104,794

(22) Filed: May 10, 2011

(65) Prior Publication Data

US 2012/0289845 A1 Nov. 15, 2012

(51) Int. Cl.
*A61B 5/04* (2006.01)
*A61N 1/00* (2006.01)
(52) U.S. Cl.
USPC ...... 600/510; 607/4; 607/5; 607/25; 600/509; 600/513; 600/515; 600/516; 600/517; 600/518
(58) Field of Classification Search
USPC .................. 607/4, 5, 25; 600/509, 510, 513, 600/515–518
See application file for complete search history.

(56) References Cited

U.S. PATENT DOCUMENTS

| 6,192,273 | B1 | 2/2001 | Igel et al. |
| 2001/0034539 | A1 | 10/2001 | Stadler et al. |
| 2004/0059237 | A1 | 3/2004 | Narayan |
| 2004/0111119 | A1 | 6/2004 | Sarkar et al. |
| 2007/0016257 | A1 | 1/2007 | Brown et al. |
| 2010/0286541 | A1 | 11/2010 | Musley |
| 2011/0319951 | A1 * | 12/2011 | More et al. ............ 607/14 |

FOREIGN PATENT DOCUMENTS

| EP | 0848965 A2 | 6/1998 |
| WO | 96/25094 A1 | 8/1996 |

OTHER PUBLICATIONS (PCT/US2012/036285) PCT Notification of Transmittal of the International Search Report and the Written Opinion of the International Searching Authority, Aug. 2012.

* cited by examiner

*Primary Examiner* — Rex R Holmes
*Assistant Examiner* — Lindsey G Hankins
(74) *Attorney, Agent, or Firm* — Michael C. Soldner

(57) ABSTRACT

A method includes retrieving electrogram (EGM) data for N cardiac cycles from a memory of an implantable medical device. N is an integer greater than 1. The method further include categorizing each of the N cardiac cycles into one of a plurality of categories based on a morphology of the N cardiac cycles and performing comparisons between pairs of the N cardiac cycles. Each of the comparisons between two cardiac cycles includes detecting a mismatch between the two cardiac cycles when the two cardiac cycles are in different categories, and detecting a match between the two cardiac cycles when the two cardiac cycles are in the same category. Additionally, the method includes classifying the rhythm of the N cardiac cycles based on a number of detected matches and detected mismatches.

17 Claims, 14 Drawing Sheets

TECHNIQUES FOR DETERMINING MORPHOLOGICAL STABILITY OF CARDIAC CYCLES

TECHNICAL FIELD

The disclosure relates to techniques for determining morphological stability of a plurality of cardiac cycles, and more particularly, to determining morphological stability of a tachyarrhythmia.

BACKGROUND

Implantable medical devices (IMDs), such as implantable cardioverter-defibrillators, may implement a variety of tachyarrhythmia detection and analysis algorithms. In some examples, IMDs may implement rate-based detection and analysis algorithms in order to detect an analyze tachyarrhythmias. IMDs may also implement template matching algorithms in order to determine the morphology of a detected tachyarrhythmia and to further classify the tachyarrhythmia. IMDs may provide therapy based on conclusions drawn from the use of these rate-based detection and template matching algorithms.

An IMD that implements a rate-based detection algorithm may monitor the length of intervals between sensed ventricular or atrial events, and detect a tachyarrhythmia when a predetermined number of those intervals are shorter than a programmed time interval. In some examples, IMDs may perform further analysis of tachyarrhythmias using rate information. For example, IMDs may characterize tachyarrhythmias based on the range of values in which the intervals fall, the stability of the intervals, and the average or median values of the intervals.

An IMD that implements a template matching algorithm may analyze the morphology of beats within a tachyarrhythmia by comparing the beats to a template that represents a particular beat morphology (e.g., a normal beat morphology). The IMD may determine whether each of the individual beats is similar or dissimilar to the template during the comparisons. After the comparisons, the IMD may identify the type of tachyarrhythmia based on how many of the beats included in the tachyarrhythmia are similar or dissimilar to the template beat morphology.

SUMMARY

An IMD of the present disclosure determines an amount of morphological similarity between a plurality of sampled cardiac cycles. In one example, the IMD may sample a plurality of cardiac cycles, categorize the plurality of cardiac cycles, compare the categories of the plurality of cardiac cycles, and identify the amount of morphological similarity between the cardiac cycles based on the comparisons. The IMD may identify the plurality of cardiac cycles as stable when a threshold amount of similarity is present between the cardiac cycles. The IMD may identify the plurality of cardiac cycles as unstable when less than the threshold amount of similarity is present between the cardiac cycles.

In some examples, the IMD may discriminate between different types of arrhythmia based on the morphological stability of cardiac cycles included in the arrhythmia. For example, the IMD may first detect a tachyarrhythmia using a rate-based detection algorithm, then the IMD may more specifically determine the type of tachyarrhythmia based on the morphological stability of the cardiac cycles included in the tachyarrhythmia. In one example, the IMD may determine that a detected tachyarrhythmia is a monomorphic ventricular tachycardia (MVT) when the detected tachyarrhythmia is determined to be morphologically stable. In another example, the IMD may determine that a detected tachyarrhythmia is a polymorphic VT (PVT) or ventricular fibrillation (VF) when the tachyarrhythmia is determined to be morphologically unstable.

IMDs may not reliably discriminate between MVT and PVT/VF based on the rate of sensed ventricular events alone, since some MVT and PVT/VF present similar rate characteristics. Accordingly, IMDs that attempt to detect tachyarrhythmias and discriminate between MVT and PVT/VF using rate information alone have the potential to mischaracterize and, therefore, mistreat a tachyarrhythmia. For example, mischaracterization and mistreatment may include providing cardioversion or defibrillation therapy to a MVT that may be more amenable to anti-tachycardia pacing (ATP) therapy. Furthermore, discriminating between tachyarrhythmias using template matching algorithms after rate-based detection may prove to be more computationally intensive and may dissipate more power than may be desirable in an IMD.

The IMD of the present disclosure that identifies tachyarrhythmia based on the morphological stability of the cardiac cycles included in a tachyarrhythmia may provide various benefits. In one example, determination of morphological stability using the categorization and comparison techniques of the present disclosure may prove to be a more accurate technique for discriminating between tachyarrhythmias than rate-based algorithms. Additionally, the categorization and comparison techniques may prove to be more computationally efficient and energy efficient than a template matching algorithm. Thus, an IMD of the present disclosure that identifies a tachyarrhythmia based on the morphological stability of the cardiac cycles included in the tachyarrhythmia may provide a computational and energy efficient solution for reliable discrimination between MVT and PVT/VF.

In some examples according to the present disclosure, a method comprises retrieving electrogram (EGM) data for N cardiac cycles from a memory of an implantable medical device. N is an integer greater than 1. The method further comprises categorizing each of the N cardiac cycles into one of a plurality of categories based on a morphology of the N cardiac cycles and performing comparisons between pairs of the N cardiac cycles. Each of the comparisons between two cardiac cycles includes detecting a mismatch between the two cardiac cycles when the two cardiac cycles are in different categories, and detecting a match between the two cardiac cycles when the two cardiac cycles are in the same category. Additionally, the method comprises classifying the rhythm of the N cardiac cycles based on a number of detected matches and detected mismatches.

In some examples according to the present disclosure, a medical device comprises a memory and a processing module. The processing module retrieves EGM data for N cardiac cycles from the memory. N is an integer greater than 1. The processing module categorizes each of the N cardiac cycles into one of a plurality of categories based on a morphology of the N cardiac cycles and performs comparisons between pairs of the N cardiac cycles. Each of the comparisons between two cardiac cycles includes detecting a mismatch between the two cardiac cycles when the two cardiac cycles are in different categories and detecting a match between the two cardiac cycles when the two cardiac cycles are in the same category. The processing module classifies the rhythm of the N cardiac cycles based on a number of detected matches and detected mismatches.

In some examples according to the present disclosure, a method comprises detecting a tachyarrhythmia based on N cardiac cycles using an implantable medical device. N is an integer greater than 1. The method further comprises categorizing each of the N cardiac cycles into one of a plurality of categories based on a morphology of the N cardiac cycles and performing comparisons between pairs of the N cardiac cycles. Each of the comparisons between two cardiac cycles includes detecting a mismatch between the two cardiac cycles when the two cardiac cycles are in different categories, and detecting a match between the two cardiac cycles when the two cardiac cycles are in the same category. Additionally, the method comprises classifying the rhythm of the N cardiac cycles as one of a monomorphic tachyarrhythmia or a polymorphic tachyarrhythmia based on a number of detected matches and detected mismatches.

In some examples according to the present disclosure, a method comprises retrieving EGM data for N cardiac cycles. N is an integer greater than 1. The method further comprises categorizing each of the N cardiac cycles into one of a plurality of categories based on a morphology of the N cardiac cycles, and performing comparisons between pairs of the N cardiac cycles. Each of the comparisons between two cardiac cycles includes detecting a mismatch between the two cardiac cycles when the two cardiac cycles are in different categories, and detecting a match between the two cardiac cycles when the two cardiac cycles are in the same category. Additionally, the method comprises classifying the rhythm of the N cardiac cycles based on a number of detected matches and detected mismatches.

The details of one or more examples are set forth in the accompanying drawings and the description below. Other features, objects, and advantages will be apparent from the description and drawings, and from the claims.

DETAILED DESCRIPTION

Figure 1:
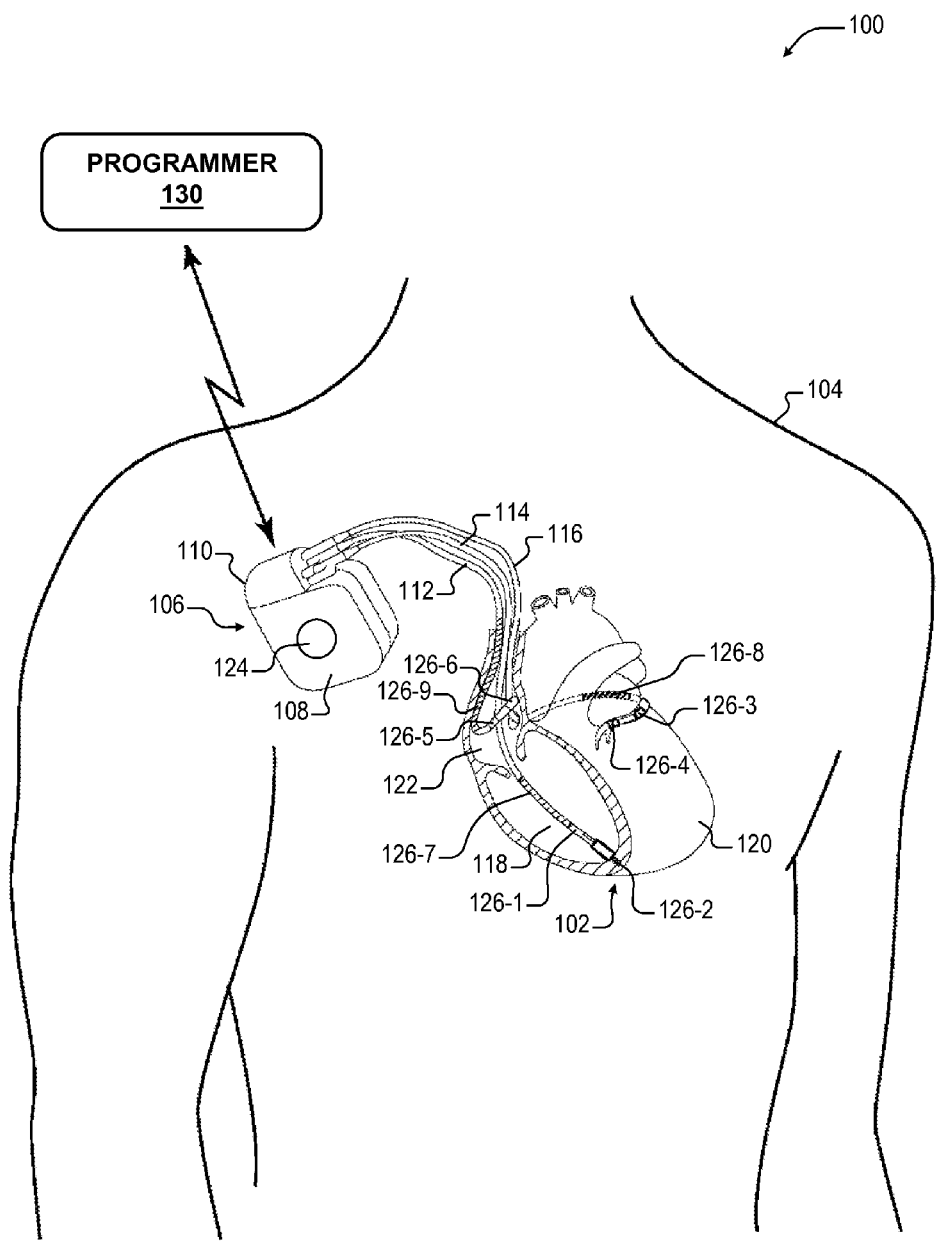
FIG. 1 is a conceptual diagram of an example system comprising an implantable medical device (IMD) for delivering stimulation therapy to a heart of a patient via implantable leads.

An IMD according to the present disclosure may determine the morphological stability of a plurality of sampled cardiac cycle electrograms (EGMs) (hereinafter "cardiac cycles"). An EGM of a cardiac cycle may include digitized data (i.e., raw data) of cardiac electrical activity that occurs from the beginning of one heartbeat to the beginning of the next heartbeat, as sensed by electrodes of the IMD. Cardiac electrical activity in a typical cardiac cycle may include a P wave, a QRS complex, a T wave, and a U wave. During a cardiac cycle, cardiac electrical activity may exhibit a baseline voltage, which may be referred to as an isoelectric line, which may be measured between a T wave of a recent cardiac cycle and a P wave of the following cardiac cycle.

Morphology of a cardiac cycle may refer to the general shape characteristics of the cardiac cycle, including, but not limited to, peak values of the cardiac cycle, slope values of the cardiac cycle, a width of the cardiac cycle, and other quantifiable features of the sampled cardiac cycle. Morphological stability of a plurality of cardiac cycles may refer to an amount of morphological similarity between the cardiac cycles. For example, a plurality of cardiac cycles that have similar shape characteristics may be referred to as morphologically stable, while a plurality of cardiac cycles that have different shape characteristics may be referred to as morphologically unstable. In general, the greater the similarity between the morphologies of the cardiac cycles, the more stable the morphology of the cardiac cycles, and the lesser the similarity between the morphologies of the cardiac cycles, the lesser the stability of the cardiac cycles (i.e., the more unstable are the cardiac cycles). The IMD of the present disclosure may quantify the morphological similarity of a plurality of cardiac cycles and may determine whether the plurality of cardiac cycles is stable or unstable based on this quantification.

In some examples, the IMD of the present disclosure may discriminate between different types of tachyarrhythmia based on whether the cardiac cycles of the detected tachyarrhythmias are morphologically stable or morphologically unstable. For example, some detected tachyarrhythmias may exhibit similar morphologies on a beat-to-beat basis (e.g., MVT), while other tachyarrhythmias may exhibit varying morphology on a beat-to-beat basis (e.g., PVT and VF). Based on this observation, the IMD may initially detect a tachyarrhythmia, e.g., using a rate-based detection algorithm, then subsequently identify the tachyarrhythmia as MVT or PVT/VF when the IMD determines that the cardiac cycles included in the tachyarrhythmia are stable or unstable, respectively. The IMD may then provide a therapy to the patient based on the type of tachyarrhythmia identified. For example, the IMD may provide ATP therapy when the tachyarrhythmia is identified as an MVT. Alternatively, the IMD may provide a cardioversion or defibrillation therapy when the tachyarrhythmia is identified as a PVT/VF.

Although the IMD may discriminate between tachyarrhythmias such as MVT and PVT/VF based on morphological stability of the tachyarrhythmia as described herein, in other examples, the IMD may discriminate between other types of arrhythmias based on the morphological stability of the arrhythmias, such as atrial fibrillation and atrial flutter. The techniques described herein may be generally applicable to comparisons of the electrical signals corresponding to ventricular activation, atrial activation, or repolarization. An intra-cardiac ventricular EGM measured from electrodes exclusively in the ventricle picks up a signal that is dominated by the electrical activation in the ventricles. Similarly, an intra-cardiac atrial EGM measured from electrodes exclusively in the atrium picks up a signal that is dominated by the electrical activation of the atrium. Beat to beat analysis of such ventricular only or atrial only activations could be used to discriminate monomorphic vs. polymorphic or fibrillatory waveforms in the ventricle and atrium respectively. Additionally, a purely subcutaneous EGM measured from subcutaneous electrodes may include both atrial and ventricular activations, and such signals may be "segmented" to extract ventricular activation and/or atrial activations. The beat-to-beat ventricular-only activations or beat-to-beat atrial-only activations could be processed to provide discrimination of monomorphic vs. polymorphic or fibrillatory rhythms in the ventricle or atrium respectively.

The IMD of the present disclosure may buffer N cardiac cycles in memory, categorize each of the N cardiac cycles into discrete categories and then perform a plurality of comparisons between the N cardiac cycles in order to determine whether the N cardiac cycles are morphologically stable or unstable. The IMD may utilize various criteria (e.g., programmable by the user) to categorize each of the N cardiac cycles into a discrete category. In one example, as described hereinafter, the IMD may categorize each of the N cardiac cycles based on the magnitude of peak points in the cardiac cycle and the order of the peak points in the cardiac cycle. In some examples, as described hereinafter, the IMD may categorize a cardiac cycle into one of 4 or more categories, including, but not limited to, a dominantly positive category, a dominantly negative category, an initially positive category, and an initially negative category.

For each of the comparisons, the IMD may determine whether the compared cardiac cycles are mismatched or matched based on the categories of the cardiac cycles being compared. The IMD may detect a mismatch between compared cardiac cycles when the cardiac cycles belong to different categories. The IMD may detect a match between cardiac cycles when the cardiac cycles are in the same category and also have another morphological attribute in common, such as a peak-to-peak amplitude, or other morphological characteristic.

After the IMD has compared a plurality of the N cardiac cycles, the IMD may determine the number of matches and mismatches between the pairs of cardiac cycles. The IMD may then determine whether the N cardiac cycles are morphologically stable or unstable based on the total number of matches and mismatches. For example, the IMD may determine that the N cardiac cycles are morphologically stable when a total number of matches is greater than a threshold number. Otherwise, the IMD may determine that the N cardiac cycles are morphologically unstable.

An example IMD 106 that acquires EGM data for a plurality of cardiac cycles, categorizes the plurality of cardiac cycles, compares the categories of the plurality of cardiac cycles, and identifies a morphological stability of the plurality of cardiac cycles based on the comparisons is now described with respect to FIGS. 1-14.

FIG. 1 shows an example system 100 that may be used to diagnose conditions of and provide therapy to a heart 102 of a patient 104. System 100 includes an IMD 106. For example, IMD 106 may be an implantable pacemaker, cardioverter, and/or defibrillator that monitors electrical activity of heart 102 and provides electrical stimulation to heart 102.

IMD 106 includes a housing 108 and a connector block 110. Housing 108 and connector block 110 may form a hermetic seal that protects components of IMD 106. IMD 106 is coupled to leads 112, 114, and 116 via connector block 110. Leads 112, 114, 116 extend into heart 102. Right ventricular lead 114 extends into right ventricle 118. Left ventricular coronary sinus lead 116 extends into the coronary sinus to a region adjacent to the free wall of left ventricle 120. Right atrial lead 112 extends into right atrium 122.

Housing 108 may enclose an electrical sensing module that monitors electrical activity of heart 102, and may also enclose a signal generator module that generates therapeutic stimulation, such as cardiac pacing pulses, ATP therapy, cardioversion therapy, and/or defibrillation therapy. Leads 112, 114, 116 are coupled to the signal generator module and the electrical sensing module of IMD 106 via connector block 110.

Figure 2:
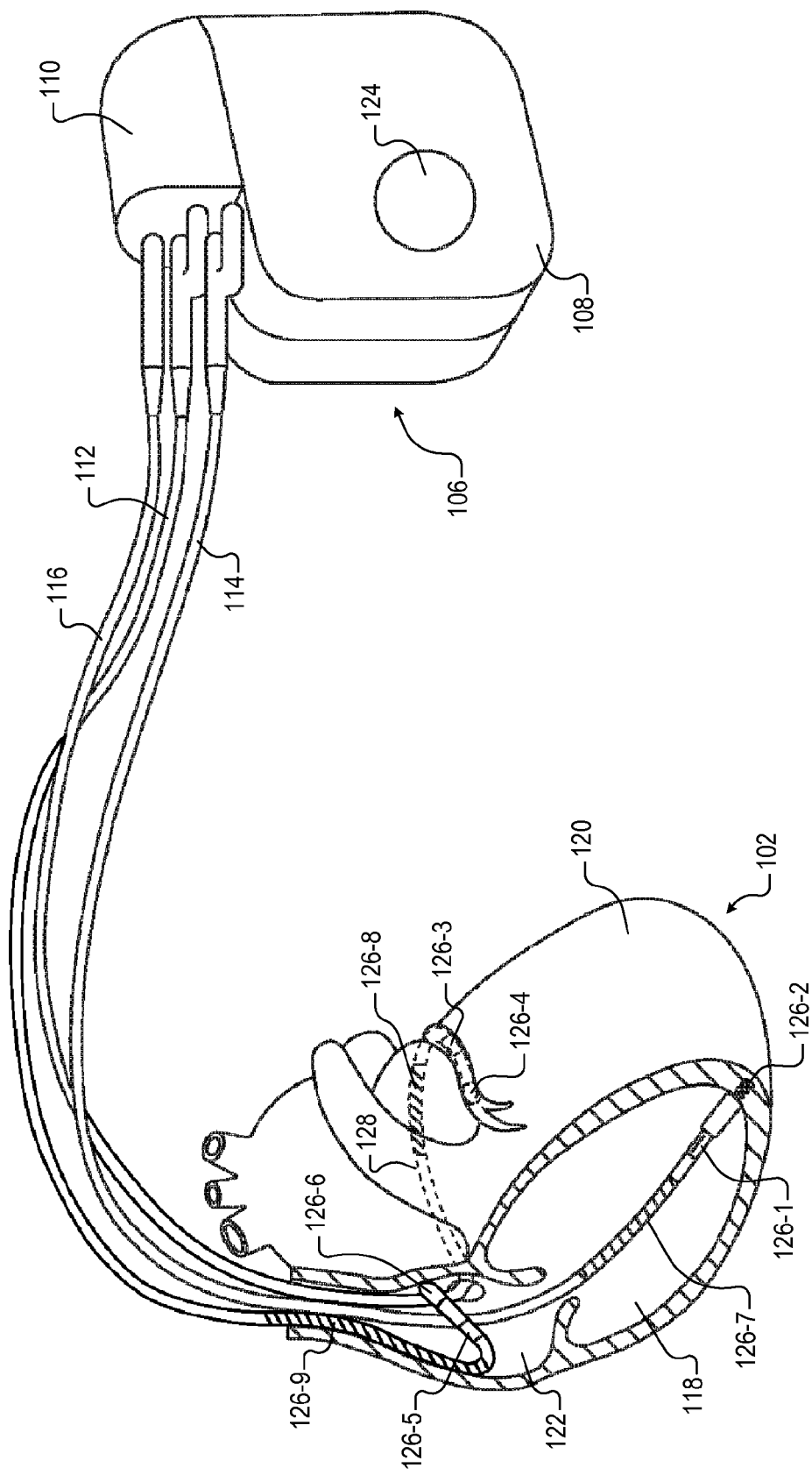
FIG. 2 shows a detailed view of the IMD and leads attached to the IMD.

FIG. 2 shows a more detailed view of IMD 106 and leads 112, 114, 116. IMD 106 includes a housing electrode 124, which may be formed integrally with an outer surface of housing 108 of IMD 106 or otherwise coupled to housing 108. Although a single housing electrode 124 is illustrated in FIGS. 1-2, IMD 106 may include more or less than a single housing electrode 124.

Leads 112, 114, 116 include electrodes 126-1-126-9 (collectively "electrodes 126"). Lead 114 includes bipolar electrodes 126-1, 126-2 which are located in right ventricle 118. Lead 116 includes bipolar electrodes 126-3, 126-4 which are located in coronary sinus 128. Lead 112 includes bipolar electrodes 126-5, 126-6 which are located in right atrium 122. Electrodes 126-1, 126-3, 126-5 may take the form of ring electrodes. Electrodes 126-2, 126-4, 126-6 may take the form of, for example, helix tip electrodes or small circular electrodes at the tip of a tined lead or other fixation element. Leads 112, 114, 116 also include elongated electrodes 126-7, 126-8, 126-9, respectively, which may take the form of a coil. Although three leads 112, 114, 116, each including three electrodes, are illustrated, other configurations of leads and electrodes are contemplated. For example, although the determination of morphological stability is described above as being performed by an implantable medical device (e.g., IMD 106) including intra-cardiac leads 112, 114, 116, in some examples, the determination of morphological stability may be performed by medical devices having subcutaneous electrodes, or a combination of subcutaneous and intra-cardiac electrodes.

IMD 106 may sense electrical activity of heart 102 and/or deliver electrical stimulation to heart 102 via electrodes 124, 126. IMD 106 may sense electrical activity using any combination of electrodes 124, 126. For example, IMD 106 may sense electrical activity via any bipolar combination of electrodes 126. Furthermore, any of electrodes 126 may be used for unipolar sensing in combination with housing electrode 124. IMD 106 may deliver pacing pulses via electrodes 124, 126 using a unipolar or bipolar combination of electrodes 124, 126. IMD 106 may deliver cardioversion pulses and/or defibrillation pulses to heart 102 via any combination of elongated electrodes 126-7, 126-8, 126-9, and housing electrode 124.

Using the signal generator module and the electrical sensing module, IMD 106 may provide pacing pulses to heart 102 based on the electrical signals sensed within heart 102. IMD 106 may also provide ATP therapy, cardioversion, and/or defibrillation therapy to heart 102 based on the electrical signals sensed within heart 102. For example, IMD 106 may detect an arrhythmia of heart 102, such as VT or VF, and deliver ATP therapy, cardioversion, or defibrillation therapy to heart 102 in response to the detection of VT/VF.

Referring back to FIG. 1, system 100 may include a programmer 130. Programmer 130 may be a handheld computing device, desktop computing device, a networked computing device, etc. Programmer 130 may include a computer-readable storage medium having instructions that cause a processor of programmer 130 to provide the functions attributed to programmer 130 in the present disclosure.

Programmer 130 may include a telemetry head (not shown). IMD 106 and programmer 130 may wirelessly communicate with one another, e.g., transfer data between one another, via the telemetry head. For example, IMD 106 may send data to programmer 130, and programmer 130 may retrieve data stored in IMD 106 and/or program IMD 106.

Data retrieved from IMD 106 using programmer 130 may include cardiac EGMs stored by IMD 106 that indicate electrical activity of heart 102. Data may also include marker channel data that indicates the occurrence and timing of sensing, diagnosis, and therapy events associated with IMD 106. Additionally, data may include information regarding the performance or integrity of IMD 106 or other components of diagnostic system 100, such as leads 112, 114, 116, or a power source of IMD 106.

Figure 7:
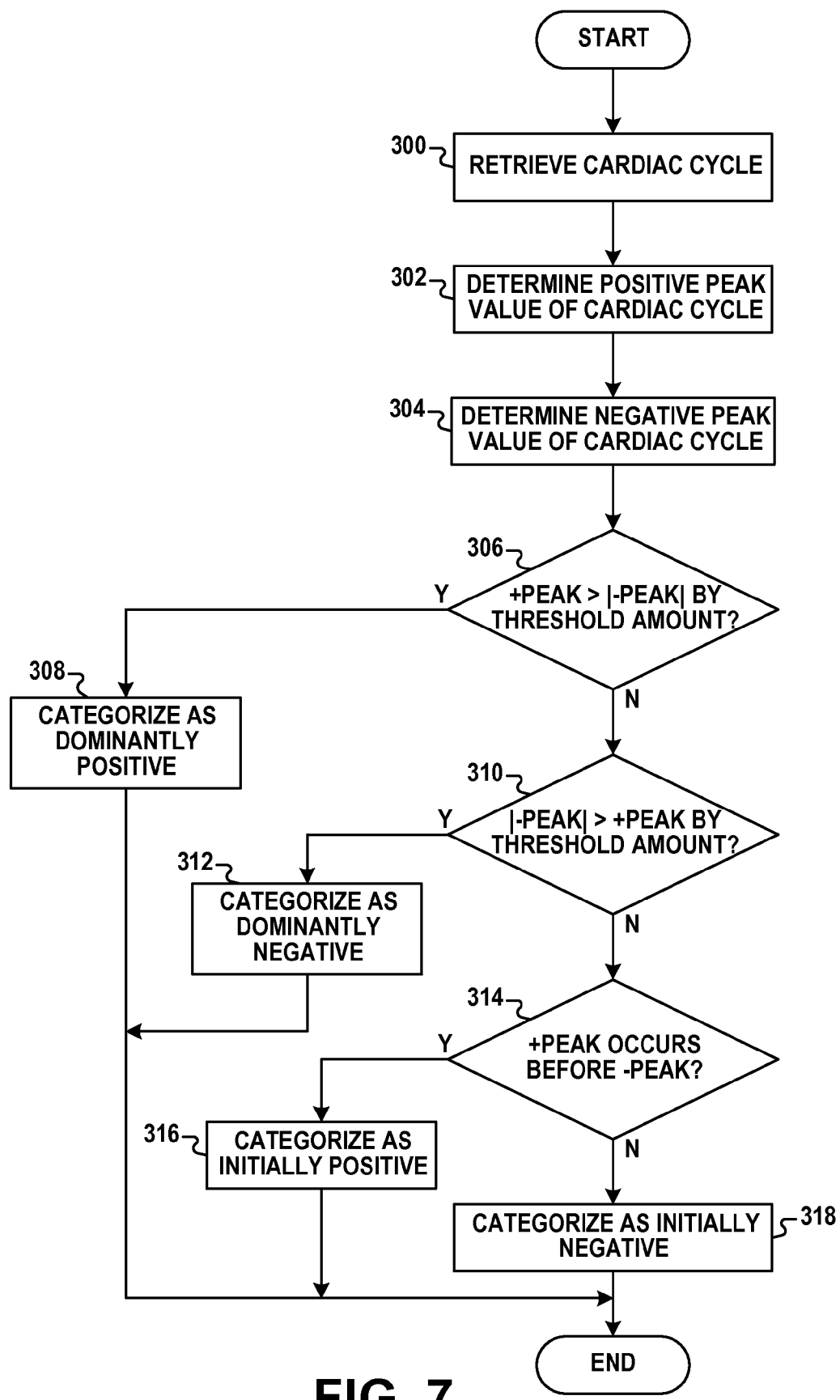
FIG. 7 illustrates an example method for categorizing a cardiac cycle.
Figure 8:
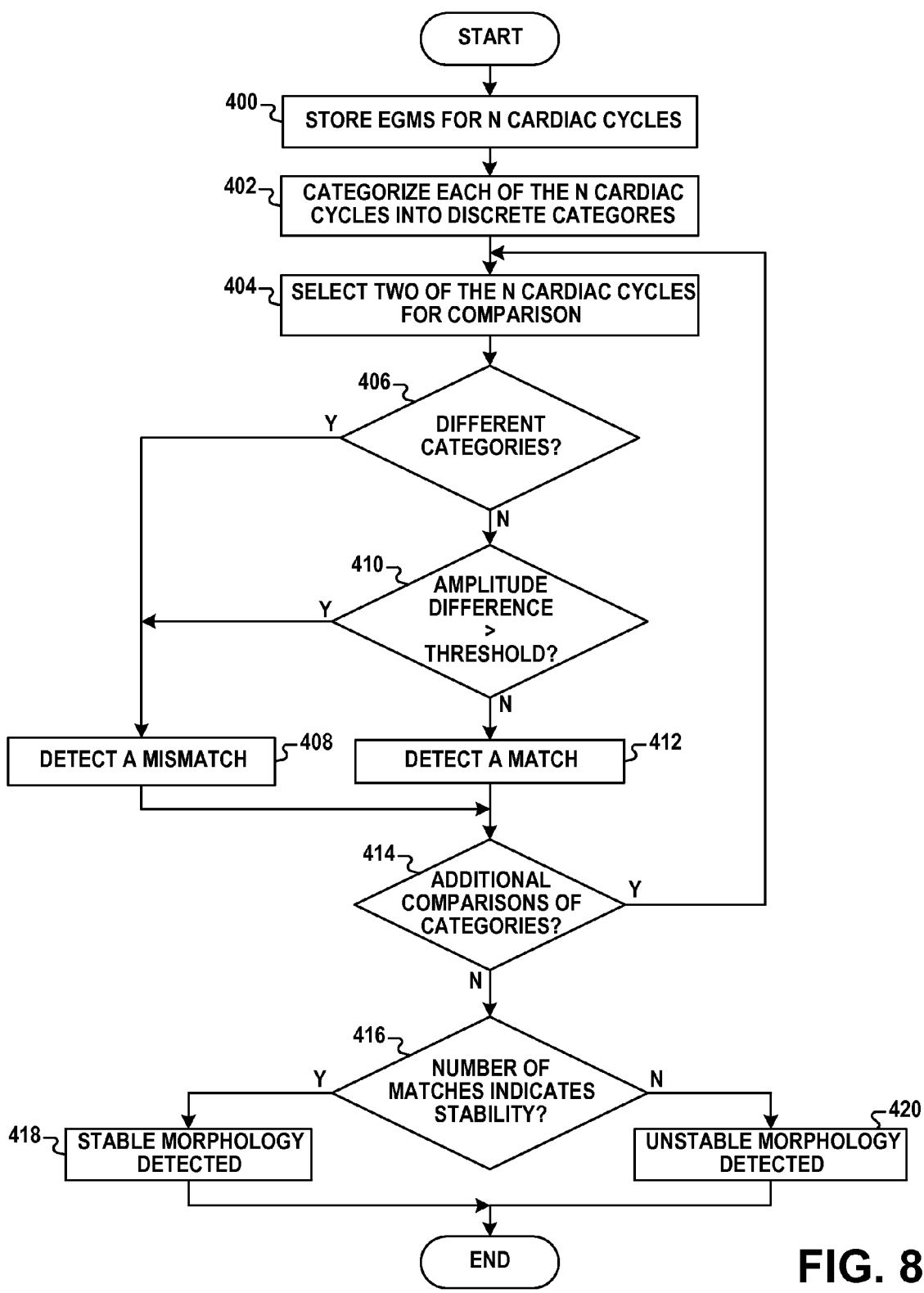
FIG. 8 illustrates an example method for comparing the morphology of N cardiac cycles and determining whether the morphology of the N cardiac cycles is stable or unstable.

Data transferred to IMD 106 using programmer 130 may include, for example, values for operational parameters, electrode selections used to deliver defibrillation pulses, waveform selections used for defibrillation pulses, and/or configuration parameters such as thresholds for characterizing and comparing cardiac cycles, as described with respect to FIG. 7 and FIG. 8.

Figure 3:
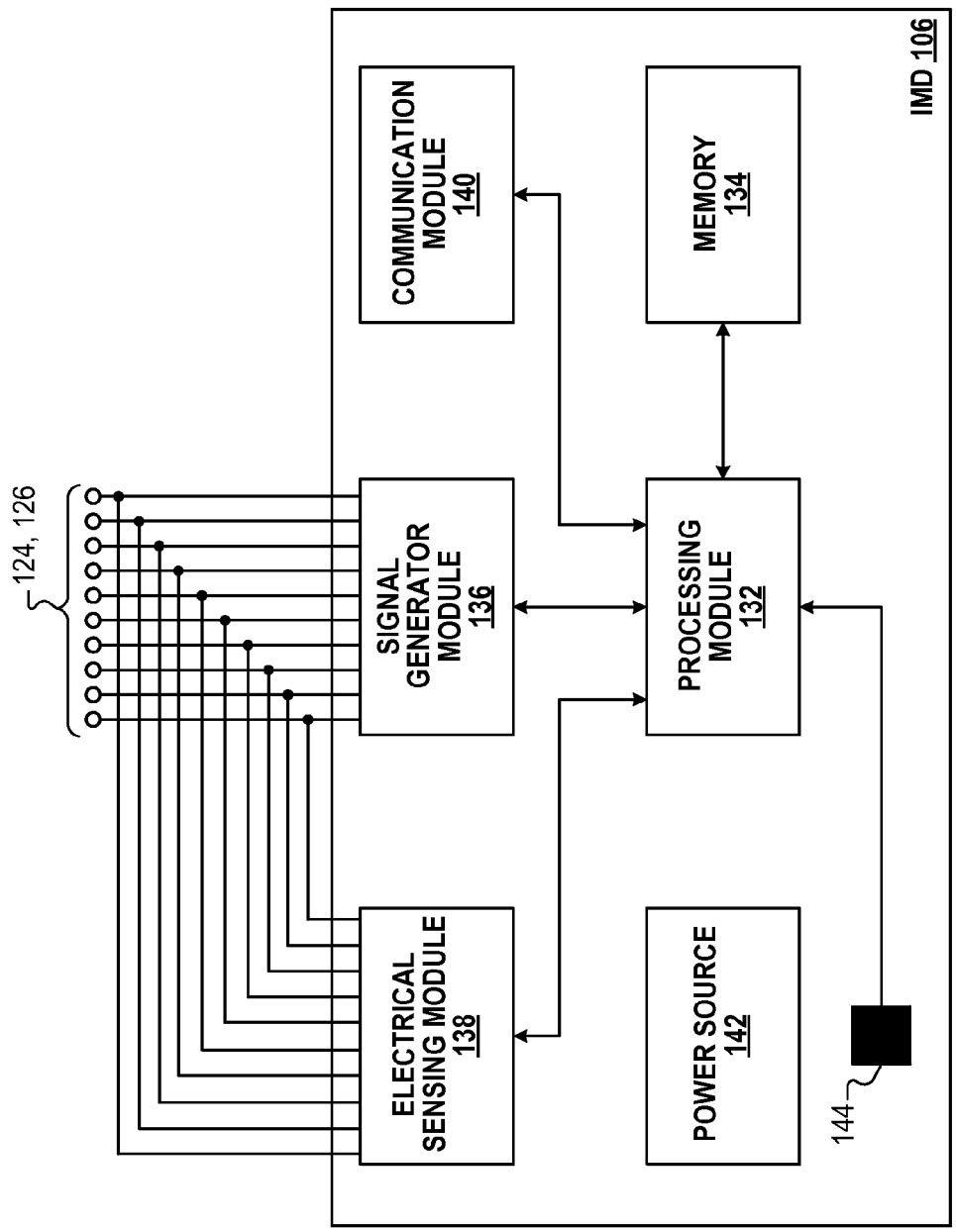
FIG. 3 shows a functional block diagram of the IMD.

FIG. 3 shows a functional block diagram of an example IMD 106. IMD 106 includes a processing module 132, memory 134, a signal generator module 136, an electrical sensing module 138, a communication module 140, and a power source 142, such as a battery, e.g., a rechargeable or non-rechargeable battery. In some examples, IMD 106 may include one or more sensors (e.g., sensor 144) with which processing module 132 may communicate. For example, sensor 144 may comprise at least one of a motion sensor (e.g., an accelerometer or piezoelectric element), a heart sound sensor, or a pressure sensor (e.g., a capacitive sensor) that senses intracardiac or other cardiovascular pressure. Processing module 132 may determine, for example, an activity level of patient 104, a heart rate, and intracardiac or other cardiovascular pressure based on data measured by sensor 144.

Modules included in IMD 106 represent functionality that may be included in IMD 106 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Processing module 132 may communicate with memory 134. Memory 134 may include computer-readable instructions that, when executed by processing module 132, cause processing module 132 to perform the various functions attributed to processing module 132 herein. Memory 134 may include any volatile, non-volatile, magnetic, or electrical media, such as random-access memory (RAM), read-only memory (ROM), non-volatile RAM (NVRAM), electrically-erasable programmable ROM (EEPROM), Flash memory, or any other digital media.

Figure 4:
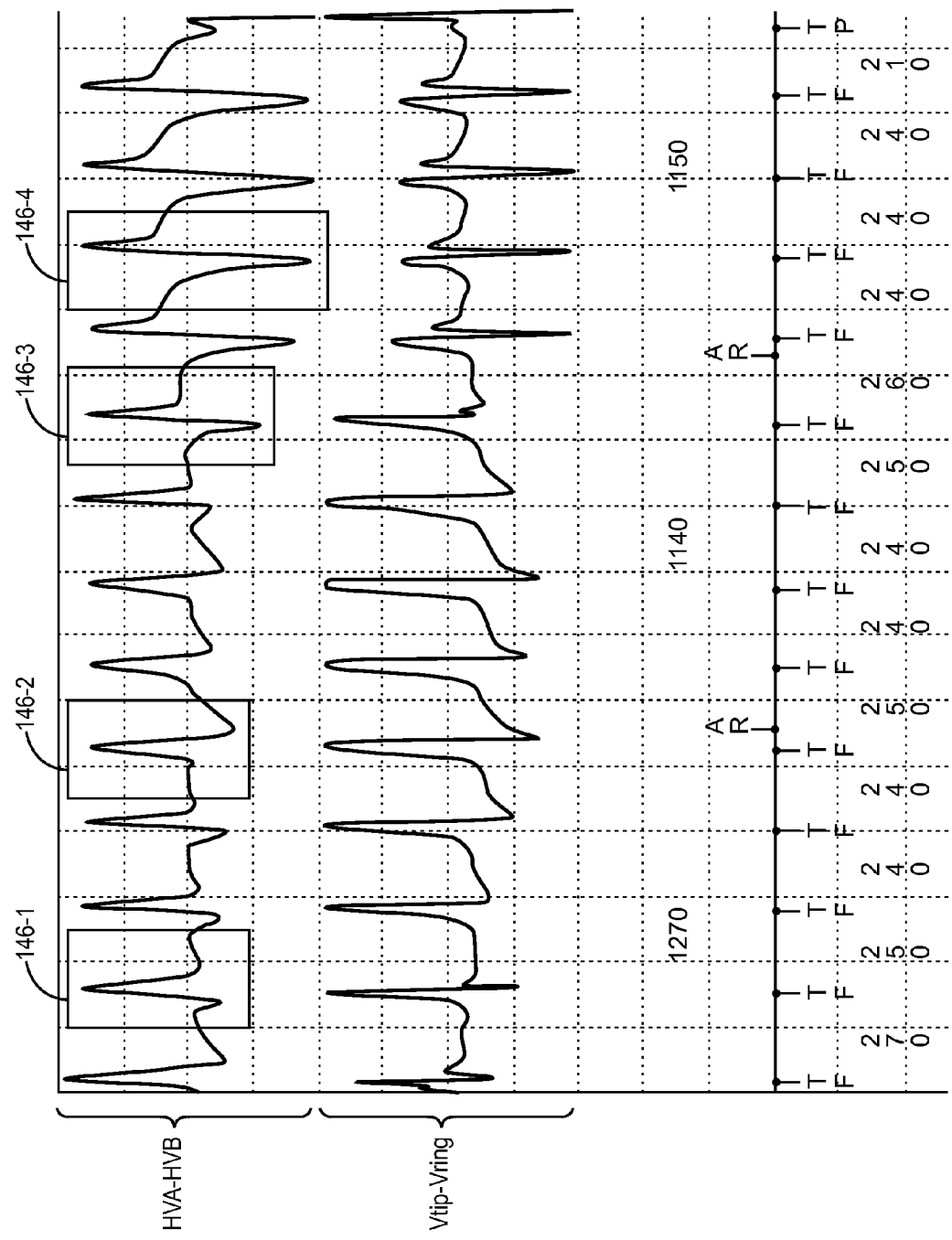
FIG. 4 shows example traces of raw data that may be generated by an electrical sensing module and processor of the IMD.

Processing module 132 may communicate with signal generator module 136 and electrical sensing module 138. Signal generator module 136 and electrical sensing module 138 are electrically coupled to electrodes 126 of leads 112, 114, 116 and housing electrode 124. Electrical sensing module 138 is configured to monitor signals from electrodes 124, 126 in order to monitor electrical activity of heart 102. Electrical sensing module 138 may selectively monitor any bipolar or unipolar combination of electrodes 124, 126. In one example, as illustrated in FIG. 4, electrical sensing module 138 may monitor electrical signals generated between electrodes 126-1, 126-2 (which may be referred to as a Vtip-Vring configuration due to the inclusion of a ventricular tip electrode and ventricular ring electrode) and electrodes 124, 126-7 (which may be referred to as HVA-HVB, with the "HV" in HVA and HVB designating "high-voltage" as electrodes 124 and 126-7 are electrodes that may be used to deliver high-voltage therapies, e.g., cardioversion or defibrillation). The electrical signals monitored between electrodes 124, 126-7 may be referred to as the far-field EGM. Although the EGMs acquired by electrical sensing module 138 are illustrated and described herein as received from electrodes 126-1, 126-2 (Vtip-Vring) and 124, 126-7 (HVA-HVB), other electrode combinations may be used to acquire EGMs for analysis according to the present disclosure.

Signal generator module 136 may generate and deliver electrical stimulation therapy to heart 102 via electrodes 124, 126. Electrical stimulation therapy may include at least one of pacing pulses, ATP therapy, cardioversion therapy, and defibrillation therapy. Processing module 132 may control signal generator module 136 to deliver electrical stimulation therapy to heart 102 according to one or more therapy programs, which may be stored in memory 134. For example, processing module 132 may control signal generator module 136 to deliver pacing pulses to heart 102 based on one or more therapy programs and signals received from electrical sensing module 138. In other examples, processing module 132 may control signal generator module 136 to deliver at least one of ATP therapy, cardioversion therapy, and defibrillation therapy when processing module 132 detects a tachyarrhythmia.

For example, in the event that processing module 132 detects a tachyarrhythmia, processing module 132 may load an ATP regimen from memory 134, and control signal generator module 136 to implement the ATP regimen. In other examples, processing module 132 may implement a cardioversion regimen or a defibrillation regimen upon detection of a tachyarrhythmia. Signal generator module 136 may include a high voltage charge circuit and a high voltage output circuit when signal generator module 136 is configured to generate and deliver defibrillation therapy to heart 102.

Communication module 140 includes any suitable hardware, firmware, software or any combination thereof for communicating with another device, such as programmer 130 and/or a patient monitor. Under the control of processing module 132, communication module 140 may receive downlink telemetry from and send uplink telemetry to programmer 130 and/or a patient monitor with the aid of an antenna (not shown) in IMD 106.

Electrical sensing module 138 may include signal conditioning circuits, e.g., amplification and filtering circuits that amplify and filter cardiac electrical signals received from electrodes 124, 126. Electrical sensing module 138 may include analog-to-digital (A/D) conversion circuits that digitize the conditioned cardiac electrical signals. The digitized data generated by the A/D circuits included in electrical sensing module 138 may be referred to as "raw data." In some examples, the A/D circuits may include an 8 bit A/D converter that samples conditioned cardiac electrical signals at approximately 256 Hz.

Processing module 132 may receive raw data from electrical sensing module 138 and detect cardiac events based on the raw data. For example, processing module 132 may analyze the raw data and detect arrhythmias (e.g., VT/VF) using any suitable arrhythmia detection algorithm. In one example, as described herein, processing module 132 may detect tachyarrhythmias using a rate based detection algorithm in which processing module 132 monitors R-R intervals and identifies a tachyarrhythmia when a predetermined ratio of R-R intervals are shorter than a threshold interval.

Processing module 132 may determine the morphological stability of a plurality of cardiac cycles based on raw data received from electrical sensing module 138. As described herein, processing module 132 may determine the morphological stability of cardiac cycles included in a tachyarrhythmia in order to more accurately identify the type of tachyarrhythmia detected. For example, processing module 132 may determine that a tachyarrhythmia detected using a rate-based method is an MVT when processing module 132 determines that the cardiac cycles leading up to the rate-based detection are morphologically stable. Processing module 132 may determine that a tachyarrhythmia detected using a rate-based method is a PVT or VF when processing module 132 determines that the cardiac cycles leading up to the rate-based detection are morphologically unstable.

Although processing module 132 may determine morphological stability of a plurality of cardiac cycles to discriminate between MVT and PVT/VF, it is contemplated that in other examples, processing module 132 may discriminate between other cardiac events using similar morphological discrimination techniques as those described herein. For example, processing module 132 may discriminate between a normally conducted ventricular beat and a premature ventricular complex (PVC).

Processing module 132 may generate marker channel data based on analysis of the raw data. Marker channel data may include data that indicates the occurrence and timing of sensing, diagnosis, and therapy events associated with IMD 106. Example marker channel data illustrated in FIG. 4 indicates sensed beats and interval lengths between beats. For example, each TF mark in FIG. 4 may indicate a sensed beat. Each TF mark may indicate that a sensed beat is within a particular interval range, in this case a fast VT range. In FIG. 4, the numbers included between the TF marks (e.g., 270, 250, 240, etc.) may indicate the length of the interval between the sensed beats, as determined by processing module 132. In the example of FIG. 4, processing module 132 may detect the sensed beats based on raw data acquired from electrodes 126-1, 126-2 (Vtip-Vring). Processing module 132 may store the generated marker channel data in memory 134. Although not illustrated, in some examples, marker channel data may include information regarding the performance or integrity of IMD 106 or other components of system 100, such as leads 112, 114, 116, or power source 142.

Processing module 132 may store raw data and marker channel data in memory 134. For example, processing module 132 may continuously store raw data from one or more electrode combinations in memory 134 as the raw data is received from electrical sensing module 138. In this manner, processing module 132 may use memory 134 as a buffer to store a predetermined amount of raw data. In some examples, processing module 132 may store raw data corresponding to a predetermined number of cardiac cycles, e.g., 12 cycles. In other examples, processing module 132 may store a predetermined number of samples of raw data, i.e., processing module 132 may stored raw data for a predetermined period of time. Processing module 132 may perform analysis on the raw data stored in memory 134. For example, analysis may include detection of tachyarrhythmia, determination of morphologic stability, generation of marker channel data, and the like, as described above.

Processing module 132 may identify and store a cardiac cycle using a variety of techniques. In one example, processing module 132 may sense an event in the cardiac cycle, such as a QRS complex (e.g., an R wave or ventricular activation), and store a window of raw data both before and after the sensed event. For example, processing module 132 may store a predetermined number of raw data points before and after the sensed event, e.g., approximately 25 data points before the event and 25 data points after the event, for a total of approximately 50 stored raw data points for each cardiac cycle. Accordingly, in some examples, each cardiac cycle stored in memory 134 may include approximately 50 raw data points. In examples where the A/D converter of electrical sensing module 138 samples cardiac electrical signals at approximately 256 Hz, processing module 132 may store approximately 200 ms of sampled cardiac electrical activity for each cardiac cycle.

FIG. 4 shows example traces of raw data that may be generated by electrical sensing module 138. As described above, the top and bottom traces illustrate electrical activity for a plurality of cardiac cycles measured between electrodes 124, 126-7 (HVA-HVB) and electrodes 126-1, 126-2 (Vtip-Vring), respectively. The top trace may be referred to as the far-field EGM.

FIG. 4 includes example cardiac cycles 146-1, 146-2, 146-3, 146-4 that may be sensed by processing module 132. Each cardiac cycle 146-1, 146-2, 146-3, 146-4 is included in a box that illustrates the boundaries of the cardiac cycle. As described above, processing module 132 may identify the boundaries of the cardiac cycles by selecting a predetermined number of sample points (e.g., 25) before and after a ventricular sensed event (e.g., an R-wave). In examples where the sensed event is an R-wave and processing module 132 stores 25 points before and after the sensed event, each stored cardiac cycle may include 50 sample points centered about a detected R-wave. Processing module 132 may continuously monitor electrodes 126-1, 126-2 (Vtip-Vring) for an R-wave, and upon detection of the R-wave, processing module 132 may store a 50 point window of the far-field EGM in memory 134. In some examples, the fiducial points used to store the sample points may be an atrial sensed event (P-wave) or a ventricular repolarization event (T-wave), and the number of sample points and the offset from the selected event may vary depending on which signal a measure of morphologic stability is desired.

Techniques for determining the morphological stability of a plurality of cardiac cycles is now described with respect to FIGS. 5-9, for example. Provisional detection of a tachyarrhythmia and subsequent discrimination of MVT and PVT/VF based on a determination of morphological stability is described with respect to FIGS. 10-12, for example.

Figure 5:
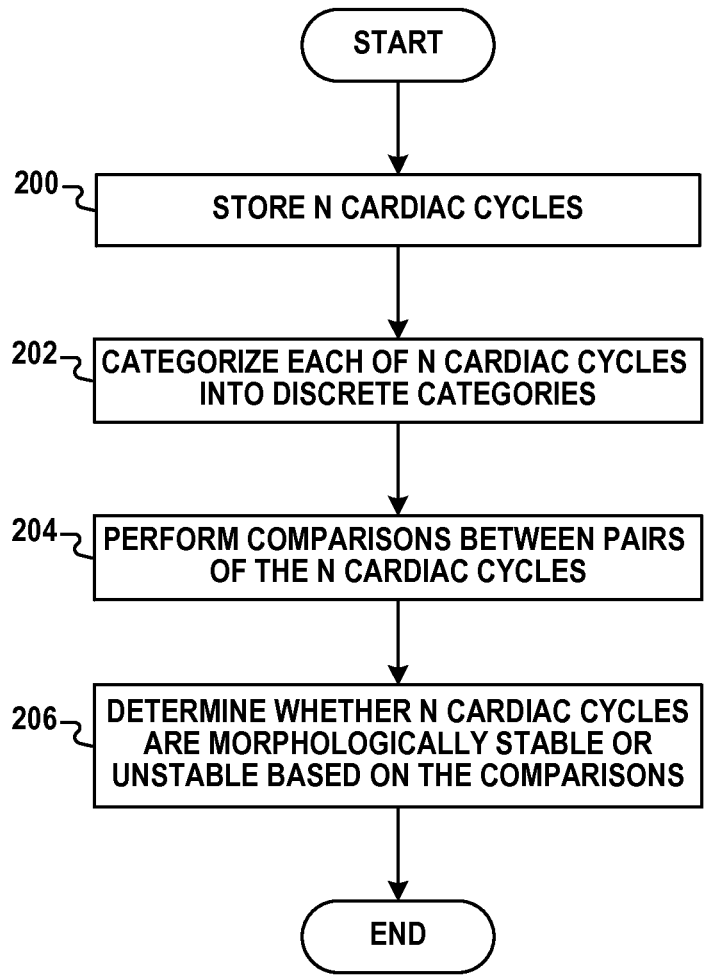
FIG. 5 shows an example method for determining whether the morphology of N cardiac cycles is stable or unstable.

FIG. 5 shows a method for determining whether the morphology of N cardiac cycles is stable or unstable. In general, a plurality of cardiac cycles may be considered morphologically stable when the plurality of cardiac cycles have similar morphologies. A plurality of cardiac cycles may be considered morphologically unstable when the plurality of cardiac cycles includes cardiac cycles having different morphologies.

During operation of IMD 106 within patient 104, processing module 132 may store (e.g., may buffer) a plurality of cardiac cycles in memory 134 (200). For example, the buffered cardiac cycles may be sampled from the far-field EGM, as described above. Processing module 132 may buffer a predetermined amount of raw data in memory 134. In the example method of FIG. 5, the predetermined amount of raw data may include N (e.g., 12) cardiac cycles.

Processing module 132 may categorize each of the N cardiac cycles into discrete categories (202). For example, processing module 132 may categorize each of the N cardiac cycles as one of a dominantly positive category, a dominantly negative category, an initially positive category, or an initially negative category. Example categorization of cardiac cycles into one of these categories is described in further detail with respect to FIGS. 6-7.

Processing module 132 performs comparisons between pairs of the N cardiac cycles (204) after categorization. In some examples, processing module 132 may perform a predetermined number of comparisons. In one example, processing module 132 may perform comparisons between all possible pairs of the N cardiac cycles, for a total of N(N-1)/2 comparisons, i.e., 66 comparisons when N is equal to 12. In other examples, processing module 132 may perform comparisons between less than all possible pairs of N cardiac cycles.

During a comparison, processing module 132 may detect a mismatch between a pair of cardiac cycles when the categories of the compared cardiac cycles are different. A mismatch may generally indicate that the pair of cardiac cycles is not morphologically similar. In some examples, processing module 132 may detect a match between a pair of cardiac cycles when the categories of the compared cardiac cycles are the same. In other examples, described herein with respect to FIG. 8, processing module 132 may detect a match between a pair of cardiac cycles when the categories of the compared cardiac cycles are the same and when an additional morphological similarity is present between the compared cardiac cycles. For example, the additional morphological similarity may be the peak-to-peak amplitudes of the compared cardiac cycles. In this example, processing module 132 may detect a match between a pair of cardiac cycles when the categories of the compared cardiac cycles are the same, and when the difference between the peak-to-peak amplitudes of the compared cardiac cycles is less than a threshold amount.

After processing module 132 performs a plurality of comparisons, processing module 132 may determine whether the N cardiac cycles are morphologically stable or morphologically unstable based on a total number of matches and a total number of mismatches between compared pairs of cardiac cycles (206). In one example, processing module 132 may determine that the cardiac cycles are morphologically stable when the percentage of matches out of the total number of comparisons is greater than a threshold percentage (e.g., greater than 70%).

Figure 6A:
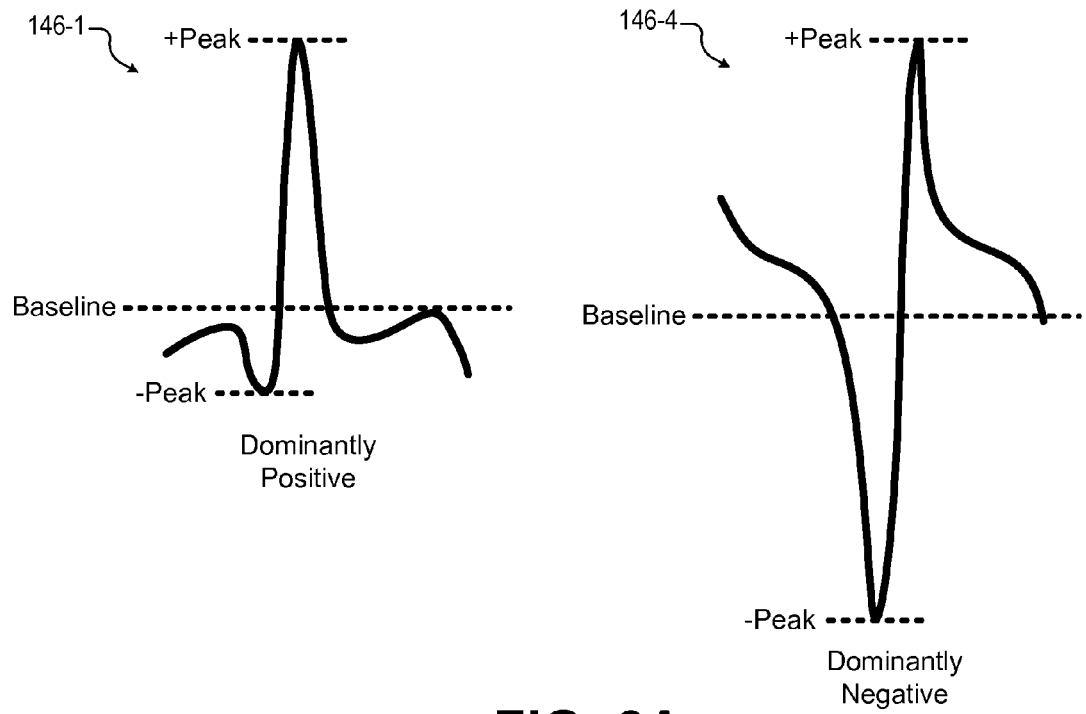
FIGS. 6A-6B illustrate example cardiac cycles that each belong to a different discrete category, namely, the dominantly positive category, the dominantly negative category, the initially positive category, and the initially negative category.
Figure 6B:
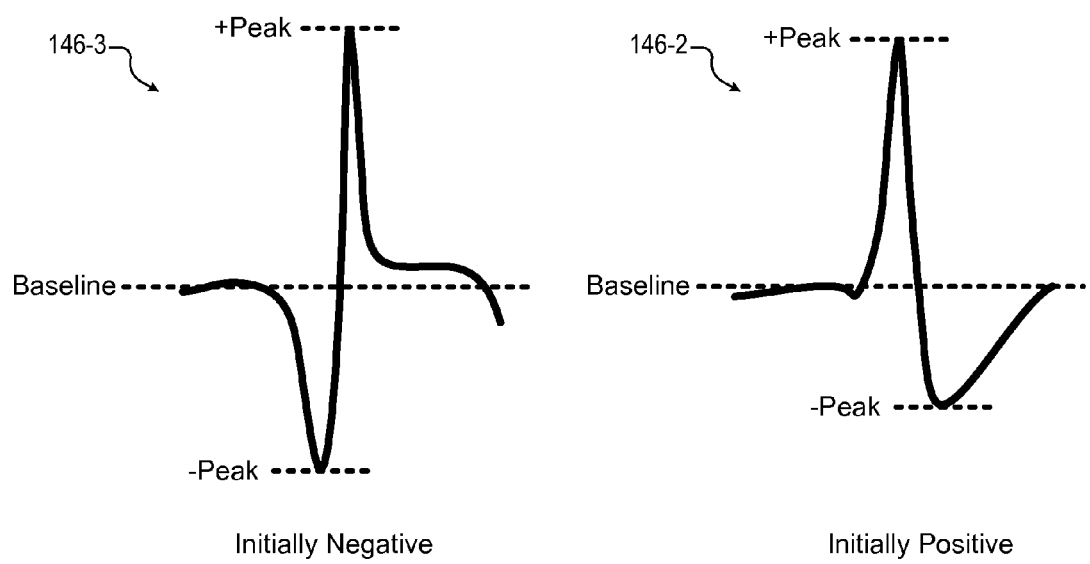

FIGS. 6A-6B illustrate example cardiac cycles 146-1, 146-2, 146-3, 146-4 that each belong to a different one of the discrete categories described above, namely, the dominantly positive category, the dominantly negative category, the initially positive category, and the initially negative category. The cardiac cycles illustrated in FIGS. 6A-6B correspond to the cardiac cycles included in FIG. 4. Although the cardiac cycles are illustrated as continuous curves, each of the cardiac cycles 146-1, 146-2, 146-3, 146-4 of FIGS. 6A-6B may represent raw data from electrical sensing module 138, e.g., cardiac cycles 146-1, 146-2, 146-3, 146-4 may represent a plurality (e.g., 50) of discretely sampled values.

Each of cardiac cycles 146-1, 146-2, 146-3, 146-4 includes a baseline level, a positive peak (indicated as +Peak), and a negative peak (indicated as −Peak). The baseline level may indicate approximately a 0V difference between electrodes 124, 126-7 (HVA-HVB). The positive peak of each of cardiac cycles 146-1, 146-2, 146-3, 146-4 may indicate the largest positive value that occurs during the cardiac cycle. The negative peak value of each of cardiac cycles 146-1, 146-2, 146-3, 146-4 may indicate the largest negative value that occurs within the cardiac cycle. Categorization of each of cardiac cycles 146-1, 146-2, 146-3, 146-4 is now described with respect to the method of FIG. 7.

FIG. 7 illustrates an example method for categorizing a cardiac cycle (e.g., cardiac cycles 146-1, 146-2, 146-3, 146-4). Processing module 132 may implement the method of FIG. 7 when categorizing each of the stored cardiac cycles. Processing module 132 may first retrieve a cardiac cycle (i.e., raw data for a cardiac cycle) from memory 134 (300). Processing module 132 may then determine the positive peak value and the negative peak value of the cardiac cycle (302), (304). For example, processing module 132 may search for the largest positive value within the cardiac cycle and the largest negative value within the cardiac cycle, then identify the largest positive and negative values as the positive peak and negative peak values, respectively.

Processing module 132 may then determine whether the positive peak value is greater than the absolute value of the negative peak value by at least a threshold amount (306). In some examples, processing module 132 may determine that the positive peak value is greater than the negative peak value by at least the threshold amount when the positive peak value is at least a fractional amount larger (e.g., 1.2 times larger) than the negative peak value. If the positive peak value is greater than the absolute value of the negative peak value by at least a threshold amount, processing module 132 may categorize the cardiac cycle as dominantly positive (308).

If the positive peak value is not greater than the absolute value of the negative peak value by at least the threshold amount, processing module 132 may determine whether the absolute value of the negative peak value is greater than the positive peak value by at least a threshold amount (310). In some examples, processing module 132 may determine that the absolute value of the negative peak value is greater than the positive peak value by at least a threshold amount if the absolute value of the negative peak value is at least a fractional amount larger (e.g., 1.2 times larger) than the positive peak value. If the absolute value of the negative peak value is greater than the positive peak value by at least the threshold amount, processing module 132 may categorize the cardiac cycle as dominantly negative (312).

Although the fractional amounts associated with the threshold amounts of blocks (306) and (310) are described as 1.2 in some examples, in other examples, the fractional amounts may be more or less than 1.2. The threshold amounts of blocks (306) and (310) may be the same in some examples, and may be different in other examples.

If the absolute value of the negative peak value is not greater than the positive peak value by at least the threshold amount, processing module 132 may determine which of the positive and negative peak values occurs first (314). If the positive peak value occurs before the negative peak value, processing module 132 may categorize the cardiac cycle as initially positive (316). If the positive peak value does not occur before the negative peak value, processing module 132 may categorize the cardiac cycle as initially negative (318).

FIG. 6A illustrates dominantly positive and dominantly negative cardiac cycles 146-1, 146-4. FIG. 6B illustrates initially positive and initially negative cardiac cycles 146-2, 146-3. With respect to cardiac cycle 146-1 of FIG. 6A, processing module 132 may determine that the positive peak value is greater than the absolute value of the negative peak value by greater than a threshold amount, as described in blocks (306) and (308), and therefore processing module 132 may categorize cardiac cycle 146-1 as dominantly positive. With respect to cardiac cycle 146-4 of FIG. 6A, processing module 132 may determine that the absolute value of the negative peak value is greater than the positive peak value by a threshold amount, as described in blocks (310) and (312), and therefore processing module 132 may categorize cardiac cycle 146-4 as dominantly negative.

With respect to cardiac cycle 146-3 of FIG. 6B, the difference between the positive peak value and the absolute value of the negative peak value may not be greater than the threshold amount, and therefore processing module 132 may not categorize cardiac cycle 146-3 as either dominantly negative or dominantly positive. Instead, processing module 132 may determine which of the positive and negative peaks occurs first. Processing module 132 may determine that the negative peak value occurs before the positive peak value according to blocks (314) and (318), and therefore processing module 132 may categorize cardiac cycle 146-3 as initially negative.

With respect to cardiac cycle 146-2 of FIG. 6B, the difference between the positive peak value and the absolute value of the negative peak value may not be greater than the threshold amount, and therefore processing module 132 may not categorize cardiac cycle 146-2 as either dominantly negative or dominantly positive. Instead, processing module 132 may determine which of the positive and negative peak values occurs first. Processing module 132 may determine that the positive peak value occurs before the negative peak value according to blocks (314) and (316), and therefore processing module 132 may categorize cardiac cycle 146-4 as initially positive.

Subsequent to categorization of a plurality of cardiac cycles according to FIG. 7, processing module 132 may perform a plurality of comparisons between pairs of categorized cardiac cycles and determine whether the plurality of cardiac cycles is morphologically stable or unstable based on the outcomes of the comparisons. A method for performing comparisons between cardiac cycles and determining whether the cardiac cycles are morphologically stable or unstable based on the comparisons is described with respect to FIGS. 8-9.

Although categorization of a cardiac cycle based on the relative magnitudes of the peak values and based on the order in which the peak values occur is described above with respect to FIG. 7, alternatively, or additionally, processing module 132 may categorize a cardiac cycle based on other morphological parameters. In some examples, processing module 132 may categorize a cardiac cycle based on at least one of the ratio of the positive and negative peak values within the cardiac cycle and the widths of lobes of the cardiac cycle. Furthermore, although only four separate categories are described with respect to FIG. 7, in some examples, processing module 132 may categorize cardiac cycles into more or less than four separate categories.

In the examples in which processing module 132 categorizes a cardiac cycle based on the ratio of positive and negative peak values, processing module 132 may first categorize a cardiac cycle based on which of the positive and negative peak values occurs first, and then further categorize the cardiac cycle based on the ratio of the larger peak to the smaller peak. In these examples, if the ratio of the peaks is greater than 6:1 and the positive peak occurs before the negative peak, the cardiac cycle may be categorized as a +6 cardiac cycle. Alternatively, if the ratio of the peaks is greater than 6:1 and the negative peak occurs before the positive peak, the cardiac cycle may be categorized as a −6 cardiac cycle. In a similar manner, if the ratio of the peaks is greater than 5:1, but less than 6:1, and the positive peak occurs before the negative peak, the cardiac cycle may be categorized as a +5 cardiac cycle. Alternatively, if the ratio of the peaks is greater than 5:1, but less than 6:1, and the negative peak occurs before the positive peak, the cardiac cycle may be categorized as a −5 cardiac cycle. In this manner, the cardiac cycle may be categorized into approximately 12 different categories (+1 to +6 and −1 to −6) based on the ratio of the larger peak to the smaller peak and based on the order in which the peaks occur.

In some examples, processing module 132 may categorize a cardiac cycle based on the widths of lobes of the cardiac cycle. Lobes may be described as disparate positive or negative sections of a the cardiac cycle waveform. In these examples, processing module 132 may first categorize a cardiac cycle based on which of the positive peak and negative peak values occurs first, and then further categorize the cardiac cycle based on the relative widths of the lobes of the cardiac cycle. If the positive peak occurs before the negative peak, and the width of the first lobe is greater than the second lobe, the cardiac cycle may be categorized as a +1 cardiac cycle. Alternatively, if the negative peak occurs before the positive peak, and the width of the first lobe is greater than the second lobe, the cardiac cycle may be categorized as a −1 cardiac cycle. If the positive peak occurs before the negative peak, and the width of the first lobe is less than the second lobe, the cardiac cycle may be categorized as a +2 cardiac cycle. However, if the negative peak occurs before the positive peak, and the width of the first lobe is less than the second lobe, the cardiac cycle may be categorized as a −2 cardiac cycle. If the positive peak occurs before the negative peak, and the width of the first lobe is approximately equal to the width of the second lobe, the cardiac cycle may be categorized as a +3 cardiac cycle. Alternatively, if the negative peak occurs before the positive peak, and the width of the first lobe is approximately equal to the width of the second lobe, the cardiac cycle may be categorized as a −3 cardiac cycle.

FIG. 8 illustrates a method for comparing the morphology of N cardiac cycles and determining whether the morphology of the N cardiac cycles is stable or unstable. As described with respect to the methods of FIG. 5 and FIG. 7, processing module 132 may store N cardiac cycles in memory 134 (402)

and categorize each of the N cardiac cycles into discrete categories (402). Processing module 132 may then select two of the N categorized cardiac cycles for comparison (404). Processing module 132 may determine whether the two selected cardiac cycles are included in the same category or in different categories (406). If processing module 132 determines that the two cardiac cycles are in different categories, processing module 132 detects a mismatch between the two cardiac cycles (408) and the method continues with block (414).

If processing module 132 determines that the two cardiac cycles are in the same category, processing module 132 compares other morphological attributes of the two selected cardiac cycles. In the example method of FIG. 8, processing module 132 compares the peak-to-peak amplitudes of the two selected cardiac cycles. The peak-to-peak amplitude of a cardiac cycle may be the difference between the positive peak value and the negative peak value of the cardiac cycle, i.e., the sum of the positive peak value and the absolute value of the negative peak value of the cardiac cycle.

Figure 9:
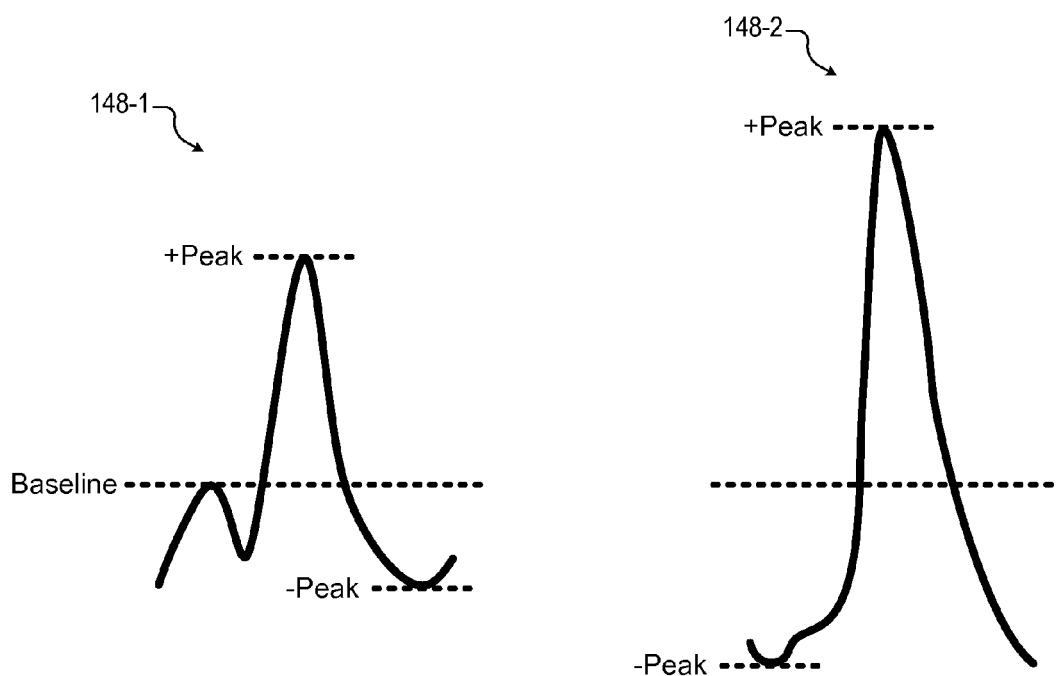
FIG. 9 illustrates an example pair of cardiac cycles that the IMD may categorize as dominantly positive but may not identify as a match.

Processing module 132 may determine whether the difference between the peak-to-peak amplitudes of the compared cardiac cycles is greater than a peak-to-peak amplitude threshold (410). The peak-to-peak amplitude threshold may be set to a percentage (e.g., 20%) of the peak-to-peak magnitude of either of the cardiac cycles being compared. Processing module 132 may detect a mismatch between the cardiac cycles of the same category if the difference between the peak-to-peak amplitudes of the cardiac cycles is greater than the peak-to-peak threshold value (408). Processing module 132 may detect a match between the cardiac cycles of the same category if the difference between the peak-to-peak amplitudes of the cardiac cycles is less than the peak-to-peak threshold value (412). FIG. 9 illustrates an example pair of cardiac cycles 148-1, 148-2 that processing module 132 may categorize as dominantly positive but may not identify as a match since cardiac cycle 148-2 may have a peak-to-peak amplitude that is greater than the peak-to-peak amplitude of cardiac cycle 148-1 by the peak-to-peak threshold value.

At block (414), processing module 132 may determine whether additional comparisons of different pairs of cardiac cycles should be made. In some examples, processing module 132 may perform a predetermined number of comparisons. For example, processing module 132 may perform an exhaustive comparison of every different pair of N cardiac cycles (i.e., N*(N-1)/2 comparisons). In other examples, processing module 132 may perform less than an exhaustive comparison of every different pair of N cardiac cycles.

If processing module 132 determines that additional comparisons are to be made, then processing module 132 may continue with block (404) and select two different cardiac cycles for comparison. If processing module 132 determines that no additional comparisons are to be made, then processing module 132 may determine whether the total number of matches indicates that the morphology of the N cardiac cycles is stable (416). In one example, processing module 132 may determine that the total number of matches indicates morphological stability when the total number of matches is greater than a threshold number of matches (418). Stated another way, processing module 132 may determine that the N cardiac cycles are morphologically stable when the total number of matches divided by the total number of comparisons (i.e., the total number of matches and mismatches) is greater than a predetermined percentage (e.g., 70%). Instead, if processing module 132 determines that the number of matches is less than the threshold number of matches, then processing module 132 may determine that the N cardiac cycles are not morphologically stable (420).

As described above, if processing module 132 determines that two cardiac cycles are in the same category, processing module 132 compares other morphological attributes of the two selected cardiac cycles. Although processing module 132 may compare peak-to-peak amplitudes of two selected cardiac cycles when the two cardiac cycles are in the same category, additionally, or alternatively, processing module 132 may compare other morphological attributes of the two selected cardiac cycles. In some examples, other morphological attributes may include, but are not limited to, most positive or most negative slopes of the two cardiac cycles, the areas or integrals of the cardiac cycles (e.g., a discrete sum), and the ratios of the values of positive and negative peaks. Accordingly, in some examples, processing module 132 may determine that two cardiac cycles are matched when the two cardiac cycles are in the same category and the most positive slopes of the cardiac cycles are within a threshold value of one another. In other examples, processing module 132 may determine that two cardiac cycles are matched when the cardiac cycles are included in the same category and the most negative slopes of the cardiac cycles are within a threshold value of one another. In still other examples, processing module 132 may determine that two cardiac cycles are matched when the cardiac cycles are included in the same category and the areas of the cardiac cycles are within a threshold value of one another. In still other examples, processing module 132 may determine that two cardiac cycles are matched when the cardiac cycles are included in the same category and the ratio of the positive and negative peak values of each cardiac cycle are within a threshold value of one another.

Figure 10:
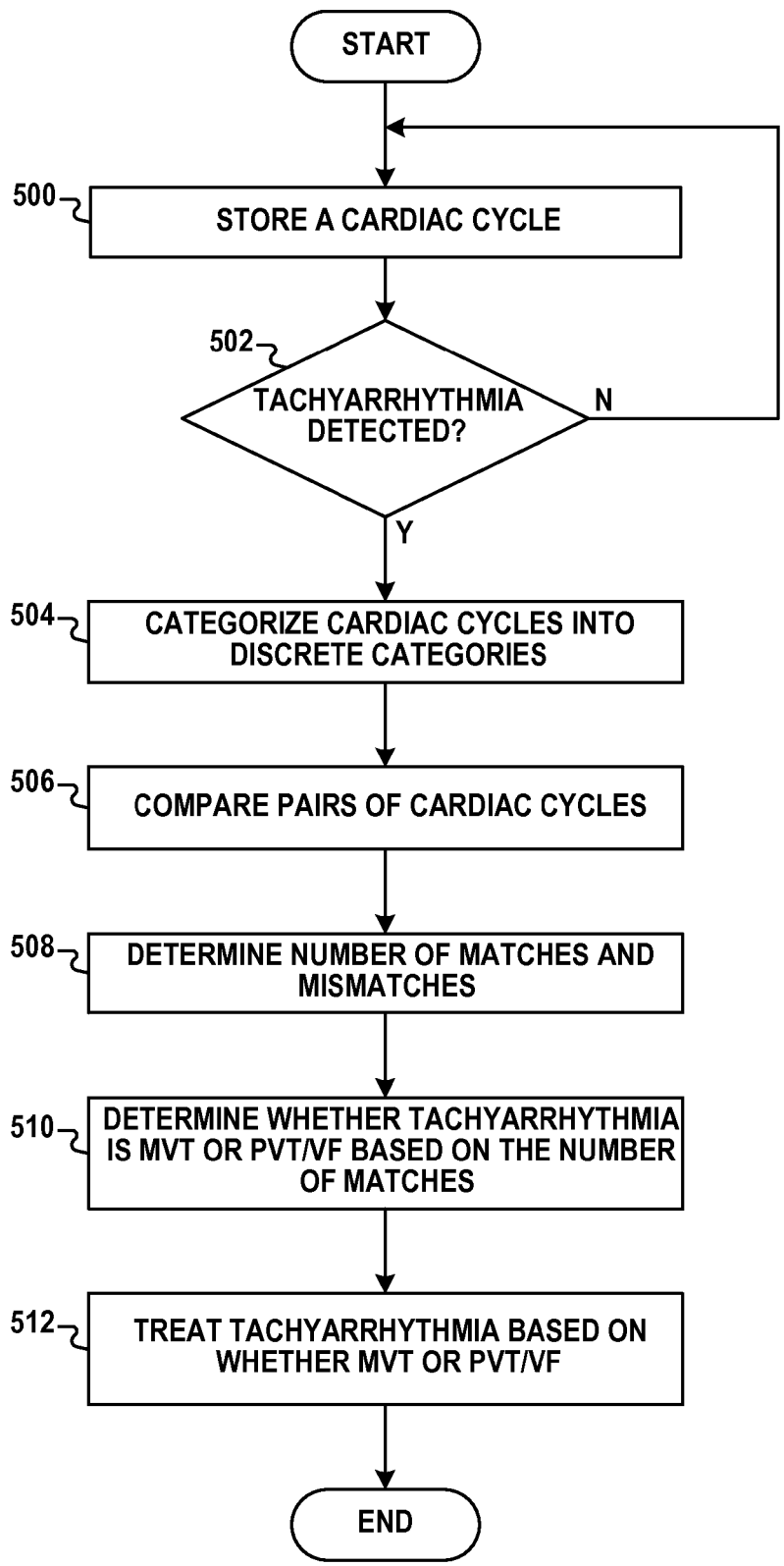
FIG. 10 illustrates an example implementation of the morphology comparison method described in FIG. 8 in which the morphology comparison method is used to determine whether a detected tachyarrhythmia is monomorphic or polymorphic.

FIG. 10 illustrates an example implementation of the morphology comparison method described in FIG. 8 in which the method is used to determine whether a detected tachyarrhythmia is an MVT or a PVT/VF. Prior to the start of the method of FIG. 10, processing module 132 may initially have stored a plurality of cardiac cycles in memory 134 during operation. For example, processing module 132 may have stored (i.e., buffered) a predetermined number of cardiac cycles (e.g., 12) in memory 134 prior to the start of the method of FIG. 10. After storing a new cardiac cycle (500), processing module 132 may determine whether patient 104 is experiencing a tachyarrhythmia (502). Processing module 132 may detect a tachyarrhythmia based on analysis of a plurality of consecutive cardiac cycles. For example, processing module 132 may detect a tachyarrhythmia using a rate-based detection algorithm in which processing module 132 monitors R-R intervals and identifies a tachyarrhythmia when a predetermined ratio of R-R intervals are shorter than a programmed threshold interval.

If a tachyarrhythmia is not detected at block (502), processing module 132 may continue to store cardiac cycles (500) and analyze raw data to detect the presence of a tachyarrhythmia. If a tachyarrhythmia is detected, processing module 132 may categorize the cardiac cycles leading up to the tachyarrhythmia detection (504). In other words, processing module 132 may categorize some or all of the cardiac cycles upon which the tachyarrhythmia determination was based. In the case where processing module 132 implements a rate-based detection method using, for example, the R-R intervals of 12 consecutive cardiac cycles, processing module 132 may categorize up to 12 of the cardiac cycles for comparison. Processing module 132 may categorize each of the cardiac cycles as one of dominantly positive, dominantly negative, initially positive, or initially negative. Processing module 132 may categorize each of the cardiac cycles as described above with respect to FIGS. 6-7.

Processing module 132 then performs comparisons of pairs of the cardiac cycles leading up to the detection of the tachyarrhythmia (506). In some examples, processing module 132 may perform a predetermined number of comparisons. During the comparisons, processing module 132 may detect either a match or a mismatch between pairs of cardiac cycles, as described with respect to FIGS. 8-9. The number of matches relative to the number of total comparisons performed by processing module 132 may indicate the type of tachyarrhythmia detected. For example, since matches between pairs of cardiac cycles indicate that the morphologies of the cardiac cycles are similar, a greater number of matches may more reliably indicate that the detected tachyarrhythmia is an MVT. On the other hand, since mismatches between pairs of cardiac cycles indicate that the morphologies of the cardiac cycles are not similar, a greater number of mismatches may more reliably indicate that the detected tachyarrhythmia is a PVT/VF.

Processing module 132 may determine a total number of matches and a total number of mismatches between compared pairs of cardiac cycles after the comparisons (508). Processing module 132 may determine that the cardiac cycles are morphologically stable, and therefore indicate MVT, when the percentage of matches out of the total number of comparisons is greater than a threshold percentage (e.g., greater than 70%) (510). Processing module 132 may determine that the cardiac cycles are morphologically unstable, and therefore indicate PVT/VF, when the percentage of matches out of the total number of comparisons is less than the threshold percentage (510).

Processing module 132 may control signal generator module 136 to deliver therapy based on whether the comparisons indicate that the tachyarrhythmia is an MVT or PVT/VF (512). In the case where the comparisons indicate that the tachyarrhythmia is an MVT, processing module 132 may control signal generator module 136 to deliver pacing termination therapy (e.g., ATP) since MVT may be reliably terminated by delivery of pacing termination therapy. In the case where the comparisons indicate that the tachyarrhythmia is a PVT/VF, processing module 132 may control signal generator module 136 to deliver cardioversion and/or defibrillation therapy since PVT/VF may be terminated reliably by delivery of cardioversion and/or defibrillation therapy.

Figure 11:
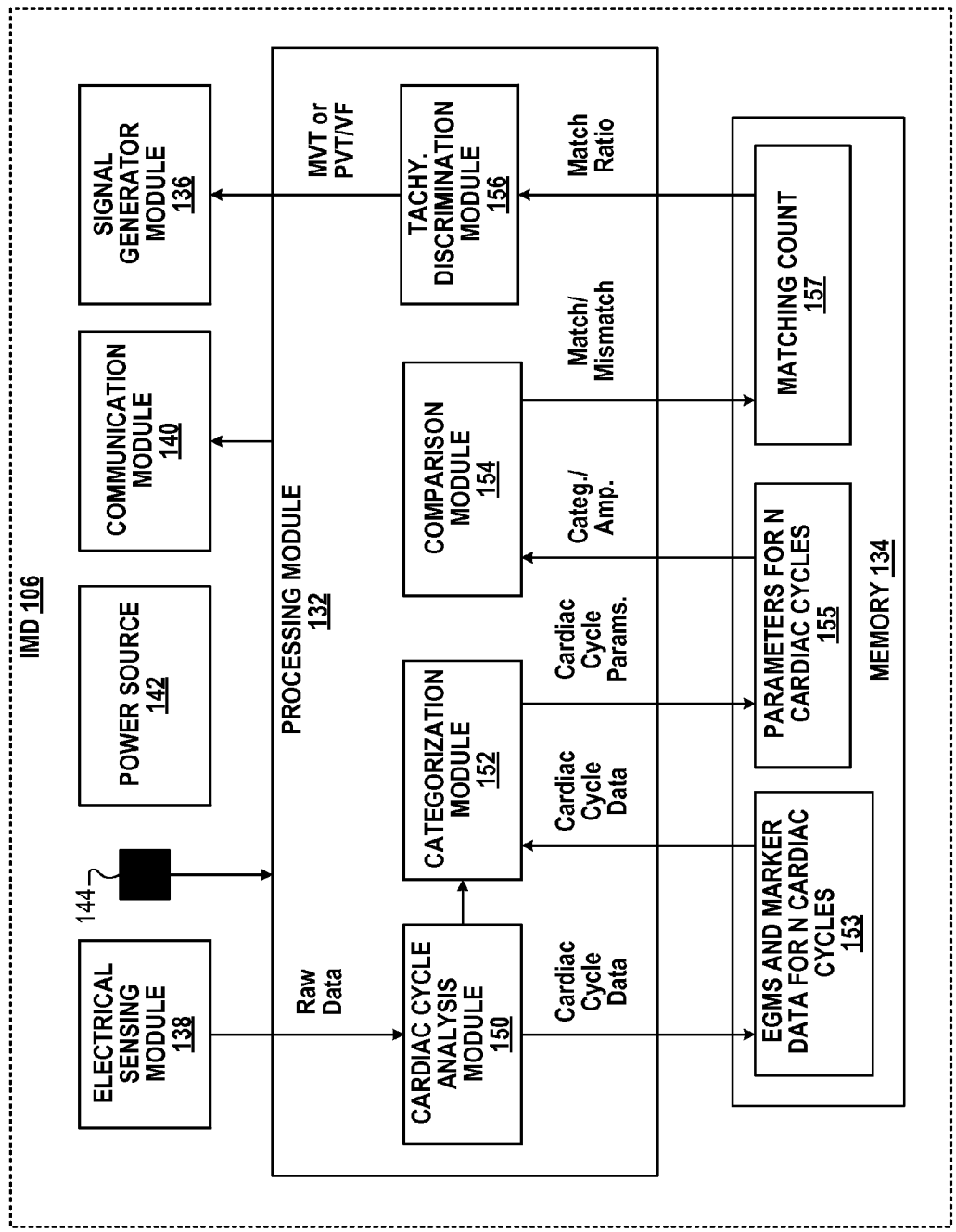
FIG. 11 is a functional block diagram of an example processing module and an example memory included in the IMD.

FIG. 11 is a functional block diagram of an example processing module 132 and an example memory 134 included in IMD 106. As described herein, example processing module 132 of FIG. 11 may implement the method of FIG. 10. Processing module 132 may include a cardiac cycle analysis module 150, a categorization module 152, a comparison module 154, and a tachyarrhythmia discrimination module 156. Memory 134 may store raw data and marker channel data for N (e.g., 12) cardiac cycles 153, parameters for N cardiac cycles 155, and a matching count 157. Raw data 153 may include signals acquired from electrodes 124, 126 (e.g., Vtip-Vring and HVA-HVB). The parameters for the N cardiac cycles 155 may include information for each of the N cardiac cycles, such as categories of the N cardiac cycles, positive peak and negative peak values, and relative timing of the positive and negative peaks of the cardiac cycles. The matching count data 157 may include the total number of matches and mismatches between compared cardiac cycles.

As described above, electrical sensing module 138 generates raw data based on cardiac electrical signals sensed via electrodes 124, 126 (e.g., HVA-HVB and Vtip-Vring). Cardiac cycle analysis module 150 buffers cardiac cycles in memory 134. Additionally, cardiac cycle analysis module 150 may analyze cardiac cycles in order to detect a tachyarrhythmia. For example, cardiac analysis module 150 may detect tachyarrhythmia using a rate-based detection algorithm, as described above.

Cardiac cycle analysis module 150 may indicate to categorization module 152 when a tachyarrhythmia is detected. Categorization module 152 may retrieve N cardiac cycles from memory 134 upon detection of the tachyarrhythmia. Categorization module 152 may then categorize each of the N cardiac cycles according to the method of FIG. 7. Categorization module 152 may store parameters determined during categorization in memory 134. For example, categorization module 152 may store the categories corresponding to each of the cardiac cycles, the positive and negative peak values corresponding to each of the cardiac cycles, and the timing of each of the cardiac cycles. The data stored by categorization module 152 may be used during comparisons of the stored cardiac cycles.

Comparison module 154 may perform comparisons between pairs of cardiac cycles in order to determine a number of matches and mismatches. Comparison module 154 may perform the comparisons based on the data stored in memory 134, e.g., the categories corresponding to each of the cardiac cycles, the positive and negative peak values corresponding to each of the cardiac cycles, and the timing of each of the cardiac cycles. Comparison module 154 may perform comparisons as described in FIGS. 8-9. Comparison module 154 may determine a number of matches and mismatches during the comparisons and store the number (i.e., matching count) in memory 134.

Tachyarrhythmia discrimination module 156 may control signal generator module 136 to deliver therapy based on the matching count. For example, tachyarrhythmia module 156 may compare the number of matches to a threshold number, and determine that the detected tachyarrhythmia is an MVT when the number of matches is greater than a threshold number, and subsequently, tachyarrhythmia discrimination module 156 may control signal generator module 136 to deliver ATP. Tachyarrhythmia discrimination module 156 may determine that the detected tachyarrhythmia is a PVT/VF when the number of matches is less than a threshold number, and subsequently, tachyarrhythmia discrimination module 156 may control signal generator module 136 to deliver cardioversion and/or defibrillation therapy.

Figure 12:
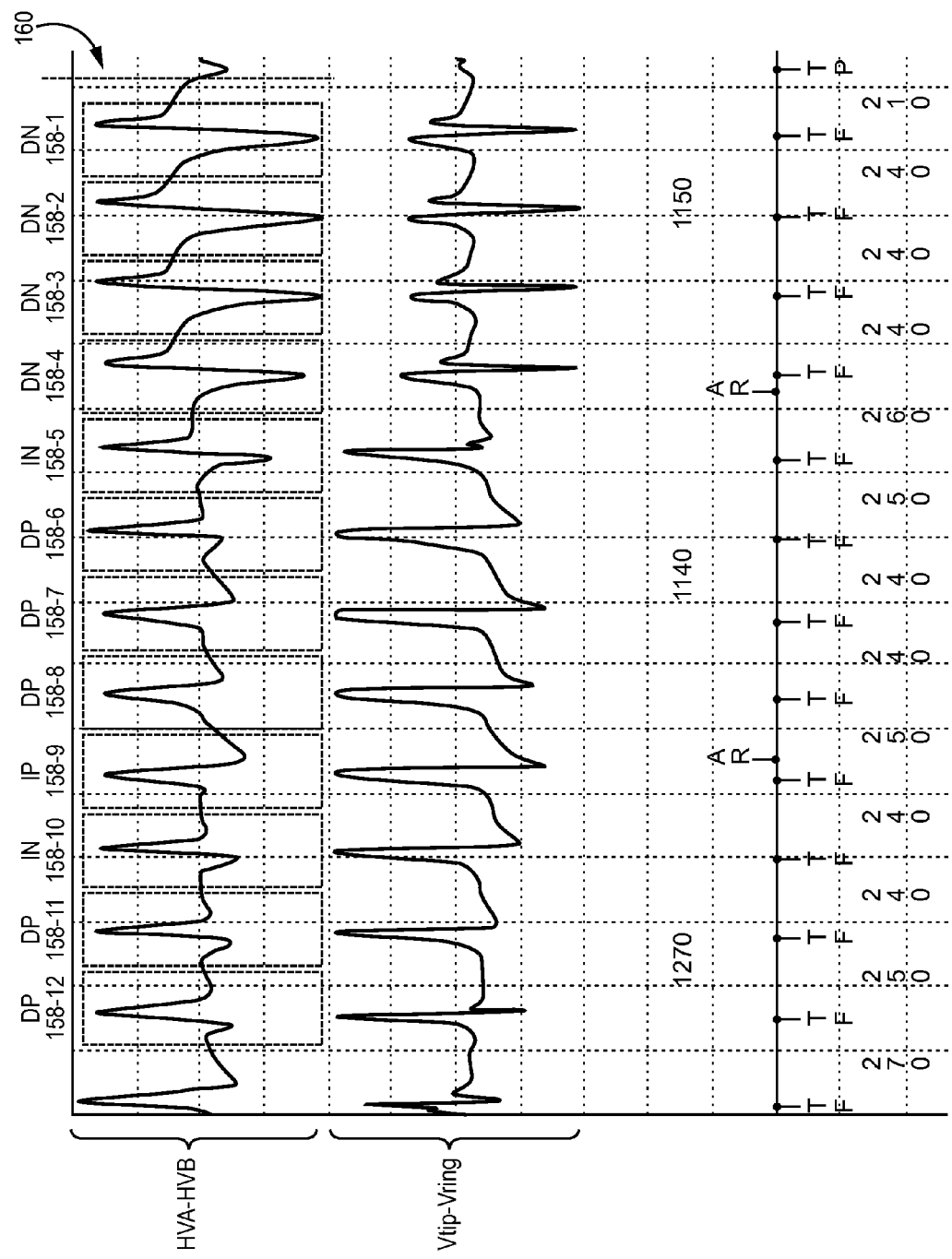
FIG. 12 shows an annotated strip chart that illustrates a plurality of cardiac cycles.

Referring now to FIG. 12, an annotated strip chart illustrates a plurality of cardiac cycles 158-1, 158-2, . . . , 158-12 (collectively "cardiac cycles 158"). Determination of the morphological stability of the twelve cardiac cycles 158 and identification of the rhythm indicated by the cardiac cycles 158 is now described using IMD 106 of FIG. 11.

Cardiac cycle analysis module 150 may detect a tachyarrhythmia at 160 after acquiring the cardiac cycles 158. For example, cardiac cycle analysis module 150 may detect a tachyarrhythmia using a rate-based detection algorithm. The short R-R intervals (e.g., 250, 240, 240, etc.), listed at the bottom of the annotated strip chart, may be indicative of a tachyarrhythmia. As such, cardiac analysis module 150 may detect the tachyarrhythmia based on analysis of the intervals in real-time, e.g., using a rate-based detection algorithm. In response to detection of the tachyarrhythmia, categorization module 152 may categorize each of the twelve cardiac cycles 158. Example categorizations of each of the cardiac cycles 158 are indicated above each of the cardiac cycles 158. DP indicates dominantly positive, DN indicates dominantly negative, IP indicates initially positive, and IN indicates initially negative.

Comparison module 154 may then perform comparisons between pairs of the cardiac cycles 158. For example, comparison module 154 may perform an exhaustive comparison of each of the pairs of cardiac cycles 158, i.e., 66 comparisons. Comparison module 154 may compare each of the categories using the method of FIG. 8, where a pair of cardiac cycles is determined to be a match when the categories of the pair of cardiac cycles is the same, and when the peak-to-peak amplitudes of the cardiac cycles are within a threshold amount of one another. In the example of FIG. 12, each of the cardiac cycles having the same categories may also have similar peak-to-peak amplitudes, i.e., peak-to-peak amplitudes within a threshold amount of one another. Therefore, in the example of FIG. 12, each of the cardiac cycles having the same category may be determined to be a match. Pairs having the same categories include (1,2), (1,3), (1,4), (2,3), (2,4), (3,4), (5,10), (6,7), (6,8), (6,11), (6,12), (7,8), (7,11), (7,12), (8,11), (8,12), and (11,12). Accordingly, comparison module 154 may determine that these cardiac cycles represent matches, for a total of 17 matches out of 66 comparisons.

In the example of FIG. 12, assuming that a threshold matching score is set to 70%, tachyarrhythmia discrimination module 156 may determine that the morphology of the twelve cardiac cycles 158 is unstable because the total number of matches is 17/66, which is less than 70%. Based on the matching score of less than 70%, tachyarrhythmia discrimination module 156 may determine that the rhythm is PVT/VF, and may control signal generator module 136 to provide cardioversion and/or defibrillation therapy.

Note that the intervals between cardiac cycles 158 are regular, i.e., the intervals have similar values. An IMD that classifies rhythms based on intervals alone may classify such a rhythm as monomorphic since the intervals are regular. Such an IMD may attempt to terminate the rhythm using ATP therapy based on such a classification, which may prove unsuccessful since the rhythm is polymorphic, and therefore, less suitable to termination using ATP. IMD 106 that implements the techniques of the present disclosure, however, may determine that the rhythm is polymorphic, and therefore may select an appropriate therapy for successfully terminating PVT, such as cardioversion and/or defibrillation.

In some examples, processing module 132 may implement a baseline drift correction technique that may correct for a drift in the baseline of the acquired cardiac cycles. A drift in the baseline of acquired cardiac cycles may refer to a scenario in which a voltage waveform (e.g., polarization buildup on electrodes) is superimposed onto the acquired cardiac cycles that may not represent physiologically significant cardiac electrical activity. In one example, such a baseline drift may add a slope to an acquired cardiac cycle. Baseline drift may cause problems with characterization of a cardiac cycle since baseline drift may cause a change in cardiac cycle amplitude, and therefore, processing module 132 may be configured to implement a baseline correction operation in order to correct for baseline drift in the acquired cardiac cycles. In some examples, baseline drifts may be observed in intra-cardiac EGMs immediately after delivery of a shock therapy to terminate a tachyarrhythmia or in intra-cardiac or subcutaneous EGM signals with inadequate filtering to prevent baseline wander due to motion artifacts, etc.

Figure 13:
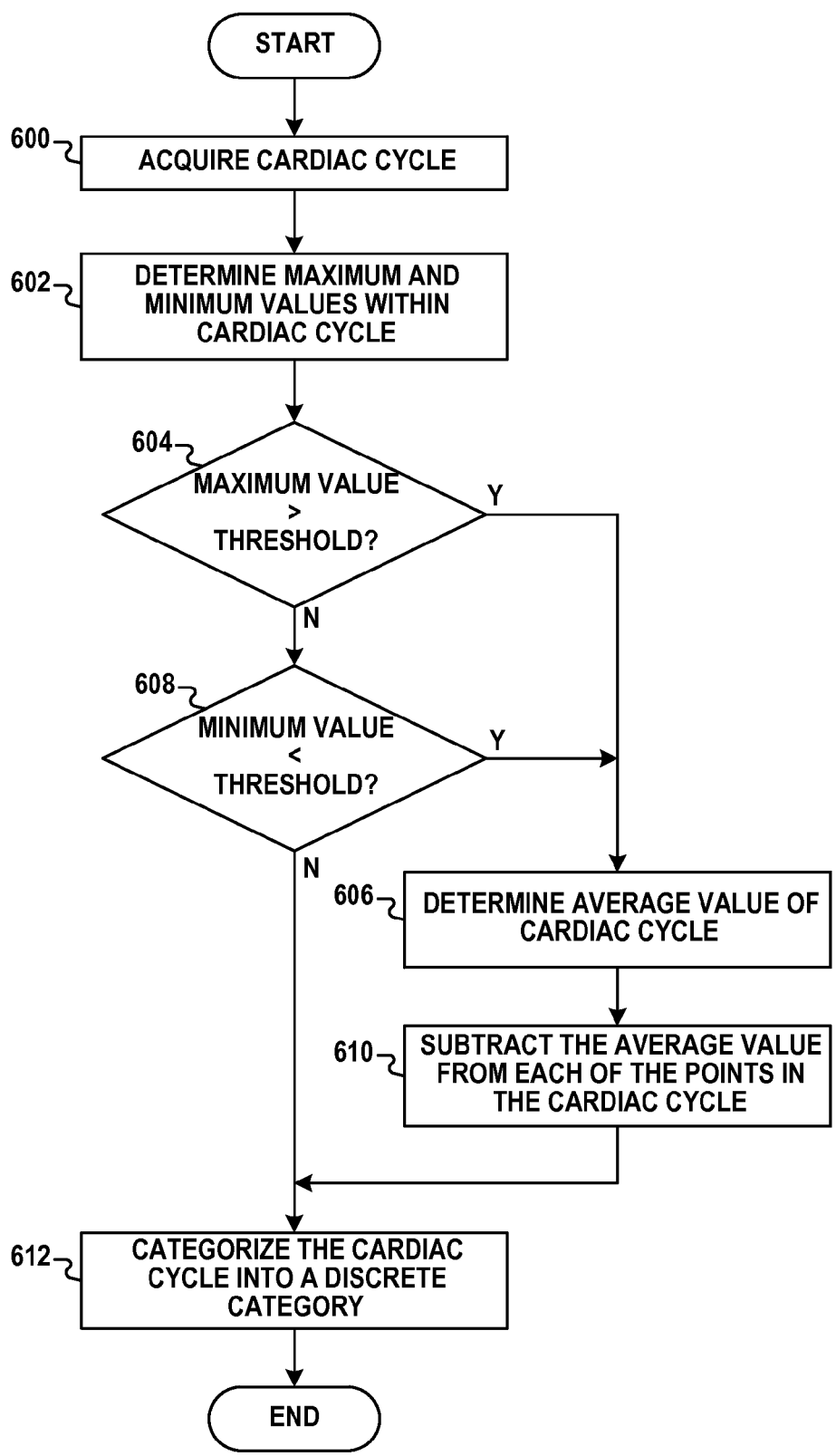
FIG. 13 illustrates an example method for correcting baseline drift.

FIG. 13 illustrates an example method for correcting baseline drift using IMD 106 of the present disclosure. The method of FIG. 13 may be implemented prior to categorization of a cardiac cycle according to, for example, block (504) of FIG. 10. Initially, cardiac cycle analysis module 150 acquires a cardiac cycle (600). Cardiac cycle analysis module 150 may then determine a maximum value (i.e., largest positive value) and a minimum value (i.e., largest negative value) within the acquired cardiac cycle (602). Cardiac cycle analysis module 150 may then determine whether the maximum value of the acquired cardiac cycle is greater than a maximum threshold value (604). If the maximum value of the cardiac cycle is greater than the maximum threshold value, the method may continue with block (606). If the maximum value of the cardiac cycle is less than the maximum threshold value, cardiac cycle analysis module 150 determines whether the minimum value of the cardiac cycle is less than a minimum threshold value (608), i.e., whether the minimum value is a larger negative value than the minimum threshold value. If the minimum value is less than the minimum threshold value, the method continues with block (608). If the minimum value is greater than the minimum threshold value, i.e., less negative than the minimum threshold value, then the values included in the cardiac cycle are within the range of the maximum and minimum values and therefore cardiac cycle analysis module 150 may not implement a baseline correction operation on the cardiac cycle.

If either the maximum value of the cardiac cycle is greater than the maximum threshold value or the minimum value of the cardiac cycle is less than the minimum threshold value, the method may continue with block (606) where cardiac cycle analysis module 150 determines an average value of the cardiac cycle (606). Cardiac cycle analysis module 150 may then subtract the average value determined in block (606) from each of the sample points in the cardiac cycle (610). Subtraction of the average value from each of the points in the cardiac cycle may eliminate baseline drift from the cardiac cycle that may adversely affect the categorization of the cardiac cycle.

Categorization module 152 may then categorize the cardiac cycle which may be free from baseline drift (612). Although elimination of baseline drift by subtraction of an average value of a cardiac cycle from each of the points of the cardiac cycle is described above, other methods of removing baseline drift from a cardiac cycle are contemplated.

Figure 14:
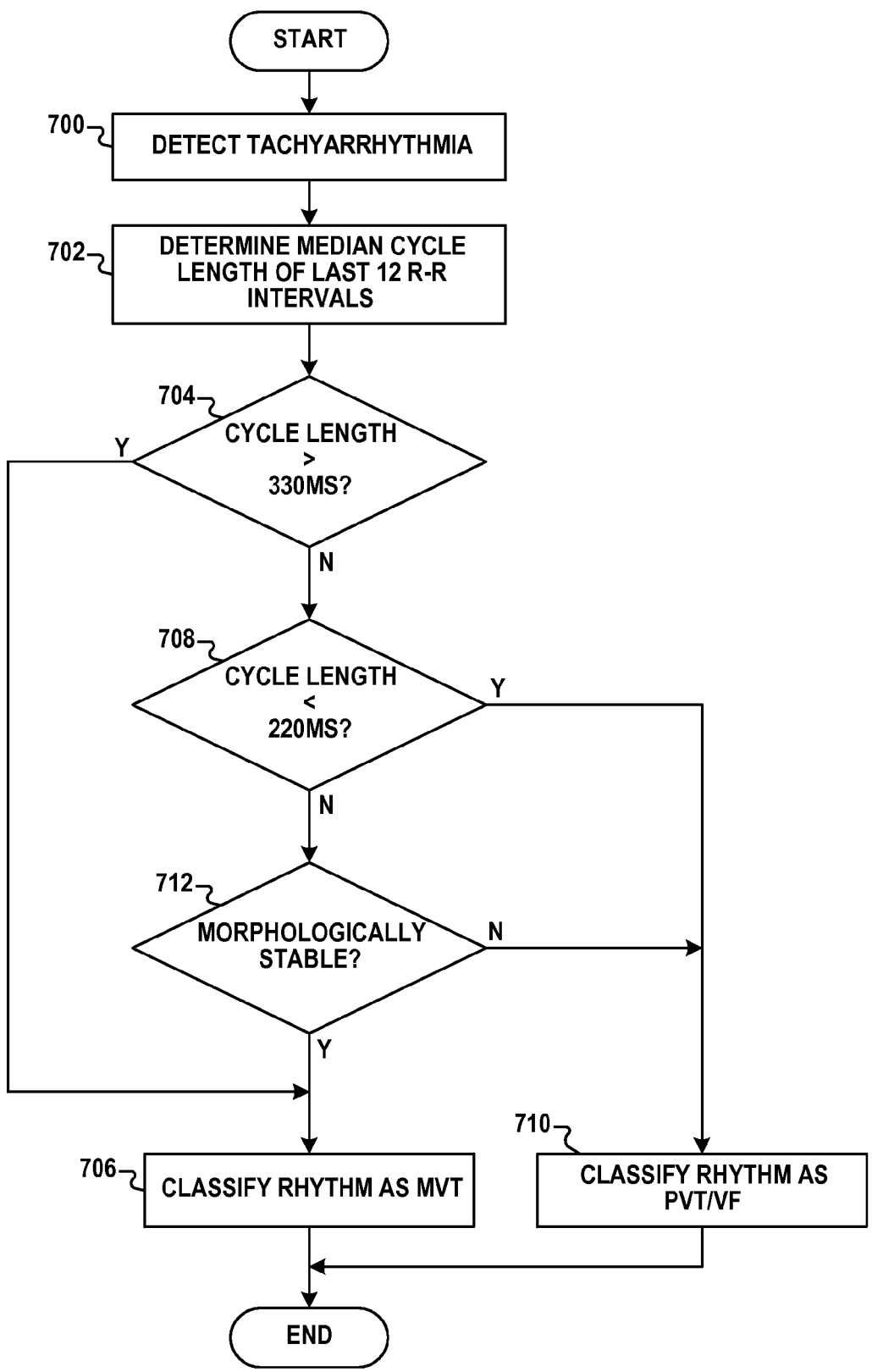
FIG. 14 illustrates an example method for using a morphological stability determination along with a cycle length analysis operation in order to determine whether rhythms are monomorphic or polymorphic.

FIG. 14 illustrates an example method for using a morphological stability determination along with a cycle length analysis operation in order to discriminate rhythms as either MVT or PVT/VF. Implementation of the method of FIG. 14 is described with respect to IMD 106 of FIG. 3. In some examples, a median cycle length of a plurality of cardiac cycles present during a tachyarrhythmia may indicate the type of tachyarrhythmia detected. In general, if a median cycle length of cardiac cycles included in a tachyarrhythmia is less than a lower threshold value (e.g., 200 ms), then the tachyarrhythmia may be classified as a PVT. If a median cycle length of cardiac cycles included in a tachyarrhythmia is greater than an upper threshold value (e.g., 330 ms), then the tachyarrhythmia may be reliably identified as an MVT. However, when the cardiac cycles included in an arrhythmia have a median cycle length between the upper and lower thresholds, the tachyarrhythmia may not be reliably identified based on the median cycle length alone. If the median cycle length falls within the range between the lower and upper thresholds (e.g., between 220 ms and 330 ms), processing module 132 may determine the morphological stability of the cardiac cycles and then determine more conclusively whether the tachyarrhythmia is an MVT or a PVT/VF based on the determination. Accordingly, as described in FIG. 14, in some examples, determining morphological stability of a plurality of cardiac cycles may be reserved for scenarios where analysis of the median cycle lengths is not conclusive. While the cycle length characterization is described as a "median" value based on 12 events, other methods, such as averaging and other window lengths may be used to characterize the tachycardia cycle length for this purpose.

Initially, processing module 132 may detect a tachyarrhythmia using a rate-based algorithm, e.g., using 12 cardiac cycles (700). Processing module 132 may then determine a median cycle length of the last 12 R-R intervals (702), i.e., the R-R intervals of the cardiac cycles leading up to detection of the tachyarrhythmia in block (700).

In general, a median cycle length of cardiac cycles leading up to detection of a tachyarrhythmia may indicate the type of tachyarrhythmia. In some examples, a median cycle length that is greater than an upper threshold value (e.g., 330 ms) may reliably indicate a tachyarrhythmia that is an MVT. In the example of FIG. 14, processing module 132 determines whether the median cycle length is greater than the upper threshold value (e.g., 300 ms) (704). If processing module 132 determines that the median cycle length is greater than 300 ms, processing module 132 may characterize the rhythm indicated by the cardiac cycles as MVT (706). If processing module 132 determines that the median cycle length is less than 300 ms, the method continues with block (708).

A median cycle length that is less than a lower threshold value (e.g., 220 ms) may reliably indicate that a tachyarrhythmia is a PVT/VF. If processing module 132 determines that the median cycle length is less than 200 ms, processing module 132 may characterize the rhythm indicated by the cardiac cycles as PVT/VF (710). If processing module 132 determines that the median cycle length is greater than 200 ms, the method continues with block (712).

A median cycle length within the range of the upper and lower threshold values may not reliably indicate either MVT or PVT/VF. In examples where processing module 132 detects a median cycle length within the range of the upper and lower threshold values, processing module 132 may determine the morphological stability of the cardiac cycles included in the median cycle length determination in order to characterize the rhythm indicated by the cardiac cycles.

As described above, e.g., with respect to FIG. 8, processing module 132 may determine whether the cardiac cycles are morphologically stable (712). If the cardiac cycles are morphologically stable, processing module 132 may classify the rhythm as MVT (706). If the cardiac cycles are morphologically unstable, processing module 132 may classify the rhythms as PVT/VF (710).

Although not illustrated in FIG. 14, processing module 132 may implement further rate and morphology discrimination algorithms after detecting a tachyarrhythmia in block 700 in order to classify the detected tachyarrhythmia as either MVT or PVT/VF. In one example, processing module 132 may implement an algorithm that looks at rate stability (e.g., the variations in the R-R intervals), e.g., between blocks (708) and (712). Such a rate stability algorithm may discriminate between different types of tachyarrhythmia based on the variations in the R-R intervals of the tachyarrhythmia, or the number of R-R intervals that fall within a certain ranges of values. A linear modesum may be one such metric of rate variability. Calculation of modesum involves grouping the cycle-lengths of the last N cardiac cycles into bins of a predefined uniform width (histogram) and computing the sum of the number of cycles in the two tallest bins. If the sum exceeds a certain threshold, generally set as a percentage of N, the rhythm satisfies rate-stability criteria. The threshold for linear modesum is varied linearly as a function of the cycle-length to allow for more variability for slower rhythms.

Although the determination of morphological stability is described above as being performed by an implantable medical device (e.g., IMD 106), in some examples, an external device may determine the morphological stability of a plurality of cardiac cycles. In one example, a computing device external to patient 104 (e.g., programmer 130 or a general purpose computer) may retrieve the plurality of cardiac cycles from IMD 106 and determine the morphological stability of the plurality of cardiac cycles retrieved from IMD 106. Although retrieving EGM data for a plurality of cardiac cycles is described above as being performed by IMD 106 (e.g., electrical sensing module 138), in other examples, cardiac cycle data may be retrieved using external electrocardiogram (ECG) electrodes attached to patient 104. For example, an ECG device may retrieve cardiac cycles via the ECG electrodes attached to patient 104. The ECG device, or other external computing device, may then determine the morphological stability of the externally sampled cardiac cycles according to the techniques of the present disclosure.

In still other examples, sampled cardiac cycles (e.g., sampled either internally or externally) may be stored and/or processed on a remote computing device, e.g., a computing device located remotely from patient 104. For example, the cardiac cycle data may be transferred via a network to a remote datastore and/or computing device. The network may include a wide area network (WAN) and/or the Internet, for example. The network may also include a shorter range network, such as a local area network (LAN). Such cardiac cycle data stored in the datastore may be retrieved at a later time by a computing device (e.g., via the network) for analysis.

Various examples have been described. These and other examples are within the scope of the following claims.

The invention claimed is:

1. A method comprising:
retrieving electrogram (EGM) data for N cardiac cycles from a memory of an implantable medical device, wherein N is an integer greater than 1;
categorizing each of the N cardiac cycles into one of a plurality of categories based on a morphology of the N cardiac cycles;
performing comparisons between pairs of the N cardiac cycles, each of the comparisons between two cardiac cycles including:
detecting a mismatch between the two cardiac cycles when the two cardiac cycles are in different categories; and
detecting a match between the two cardiac cycles when the two cardiac cycles are in the same category; and
classifying the rhythm of the N cardiac cycles based on a number of detected matches and detected mismatches, wherein categorizing each of the N cardiac cycles comprises categorizing a single cardiac cycle of the N cardiac cycles based on at least one of a positive peak value of the single cardiac cycle, a negative peak value of the single cardiac cycle, and an order in which the positive peak value and the negative peak value occur in the single cardiac cycle, and further comprising:
categorizing the single cardiac cycle as a dominantly positive cycle when the positive peak value is greater than the absolute value of the negative peak value by a first threshold amount; and
categorizing the single cardiac cycle as a dominantly negative cycle when the absolute value of the negative peak value is greater than the positive peak value by a second threshold amount.

2. The method of claim 1, wherein the implantable medical device includes at least one of a pacemaker and a cardioverter-defibrillator.

3. The method of claim 1, further comprising categorizing the single cardiac cycle as one of initially positive or initially negative when the positive peak value is not greater than the absolute value of the negative peak value by the first threshold amount and when the absolute value of the negative peak value is not greater than the positive peak value by the second threshold amount.

4. The method of claim 3, wherein categorizing the single cardiac cycle as initially positive comprises determining that the positive peak value occurs before the negative peak value in the single cardiac cycle, and wherein categorizing the single cardiac cycle as initially negative comprises determining that the negative peak value occurs before the positive peak value in the single cardiac cycle.

5. The method of claim 1, wherein performing comparisons between pairs of the N cardiac cycles comprises performing $N*(N-1)/2$ comparisons.

6. The method of claim 1, wherein classifying the rhythm comprises:
classifying the rhythm as a monomorphic ventricular tachycardia when the number of detected matches is greater than or equal to a threshold number of matches; and
classifying the rhythm as at least one of a polymorphic ventricular tachycardia or ventricular fibrillation when the number of detected matches is less than the threshold number of matches.

7. The method of claim 1, wherein each of the comparisons between the two cardiac cycles includes detecting a match between the two cardiac cycles when the two cardiac cycles are in the same category and the two cardiac cycles have a second quantifiable morphological similarity.

8. The method of claim 7, wherein the second quantifiable morphological similarity is a peak-to-peak amplitude, and wherein each of the comparisons between the two cardiac cycles includes detecting a match between the two cardiac cycles when the two cardiac cycles are in the same category and when a difference in the peak-to-peak amplitudes of the two cardiac cycles is less than a threshold amplitude.

9. The method of claim 7, wherein the second quantifiable morphological similarity includes slope values of the two cardiac cycles, areas of the two cardiac cycles, and ratios of peak values of the two cardiac cycles.

10. The method of claim 1, wherein N is an integer greater than or equal to 12.

11. A medical device comprising:
a memory; and
a processing module configured to:
retrieve electrogram (EGM) data for N cardiac cycles from the memory, wherein N is an integer greater than 1;
categorize each of the N cardiac cycles into one of a plurality of categories based on a morphology of the N cardiac cycles;
perform comparisons between pairs of the N cardiac cycles, each of the comparisons between two cardiac cycles including:
detecting a mismatch between the two cardiac cycles when the two cardiac cycles are in different categories; and
detecting a match between the two cardiac cycles when the two cardiac cycles are in the same category; and
classify the rhythm of the N cardiac cycles based on a number of detected matches and detected mismatches, wherein the processing module is configured to categorize a single cardiac cycle of the N cardiac cycles based on at least one of a positive peak value of the single cardiac cycle, a negative peak value of the single cardiac cycle, and an order in which the positive peak value and the negative peak value occur in the single cardiac cycle, and wherein the processing module is configured to:
categorize the single cardiac cycle as a dominantly positive cycle when the positive peak value is greater than the absolute value of the negative peak value by a first threshold amount; and
categorize the single cardiac cycle as a dominantly negative cycle when the absolute value of the negative peak value is greater than the positive peak value by a second threshold amount.

12. The medical device of claim 11, further comprising a housing configured to be implanted in a patient, wherein the housing houses the memory and the processing module.

13. The medical device of claim 11, wherein the processing module is configured to categorize the single cardiac cycle as one of initially positive or initially negative when the positive peak value is not greater than the absolute value of the negative peak value by the first threshold amount and when the absolute value of the negative peak value is not greater than the positive peak value by the second threshold amount.

14. The medical device of claim 13, wherein the processing module is configured to categorize the single cardiac cycle as initially positive when the positive peak value occurs before the negative peak value in the single cardiac cycle, and wherein the processing module is configured to categorize the single cardiac cycle as initially negative when the negative peak value occurs before the positive peak value in the single cardiac cycle.

15. The medical device of claim 11, wherein the processing module is configured to:
classify the rhythm as a monomorphic ventricular tachycardia when the number of detected matches is greater than or equal to a threshold number of matches; and
classify the rhythm as one of a polymorphic ventricular tachycardia and ventricular fibrillation when the number of detected matches is less than the threshold number of matches.

16. The medical device of claim 11, wherein each of the comparisons between the two cardiac cycles includes detecting a match between the two cardiac cycles when the two cardiac cycles are in the same category and the two cardiac cycles have a second quantifiable morphological similarity.

17. The medical device of claim 16, wherein the second quantifiable morphological similarity is a peak-to-peak amplitude, and wherein each of the comparisons between the two cardiac cycles includes detecting a match between the two cardiac cycles when the two cardiac cycles are in the same category and when a difference in the peak-to-peak amplitudes of the two cardiac cycles is less than a threshold amplitude.

* * * * *